(12) United States Patent
Brooks et al.

(10) Patent No.: US 7,705,049 B2
(45) Date of Patent: Apr. 27, 2010

(54) METHODS FOR TREATING NON-MELANOMA CANCERS WITH PABA

(75) Inventors: Peter C. Brooks, Carmel, NY (US); Leonard Liebes, New Rochelle, NY (US); Elissa Kramer, New York, NY (US); Bruce Ng, New York, NY (US); Danielle Morais, Putnam Valley, NY (US)

(73) Assignee: New York University, New York, NY (US)

( * ) Notice: Subject to any disclaimer, the term of this patent is extended or adjusted under 35 U.S.C. 154(b) by 840 days.

(21) Appl. No.: 11/044,638

(22) Filed: Jan. 20, 2005

(65) Prior Publication Data

US 2005/0220705 A1 Oct. 6, 2005

Related U.S. Application Data

(60) Provisional application No. 60/538,359, filed on Jan. 21, 2004.

(51) Int. Cl.
*A61K 31/192* (2006.01)

(52) U.S. Cl. .................................................. 514/557
(58) Field of Classification Search .................. 514/557
See application file for complete search history.

(56) References Cited

U.S. PATENT DOCUMENTS 3,019,165 A * 1/1962 Mansor ...................... 514/161
4,762,705 A * 8/1988 Rubin ........................ 424/85.4
4,853,221 A 8/1989 Elslager et al.
5,887,215 A 3/1999 Earle et al.

FOREIGN PATENT DOCUMENTS

WO WO-2004/058241 7/2004

OTHER PUBLICATIONS

Langdon et al. Annals of Oncology, 1994, vol. 5, No. 5, pp. 415-422 (Abstract attached).*
Biffi et al. Anticancer Research, 1998, vol. 18, No. 6A, pp. 4109-4114 (Abstract attached).*
Hughes, C.G. Journal of the American Academy of Dermatology, 1983, vol. 9, No. 5, p. 770.*
Sausville et al. Cancer Research, 2006, vol. 66, pp. 3351-3354.*
Johnson et al. British J. of Cancer, 2001, 84(10):1424-1431.*
Database HCAPLUS on STN Online, No. 1994:71152, Esposito et al., 'Para-Ambinobenzoic Acid Suppression of Cis-Fiam-minedichloroplatinum (II) Nephrotoxicity', abstract, Carcinogenesis, 1993, vol. 14, No. 12, pp. 2595-2599.
Database MEDLINE on STN Online, No. 96271360, Esposito et al., 'Effect of Para-Aminobenzoic Acid on the Pharmacokinetics and Urinary Excretion of Cis-Diamminedichloroplatinum (II) in Rats,' abstract, Anticancer Research, 1994, vol. 15, No. 6B, pp. 2541-2547.
Aisner et al., Cancer Treat Rep. 1982;66(2):221-230.
Allen et al., Crit Rev Oncol Hematol. 2001;39(1-2):139-146.
Alverez et al., Clin Cancer Res. 2002;8(9):2806-2811.
Breast Cancer Trialists' Collaborative Group, Lancet. 1998;351(9114):1451-1467.
Cagnoni et al., Cancer Detection and Prevention 1998;22(Supplement 1):S226.
Clarke et al., Clin Cancer Res. 2000;6:3621-3628.
Gold et al., Clin Cancer Res. 2003;9(10 Pt 2):3929S-3937S.
Coiffier et al., N Engl J Med. 2002;346(4):235-242.
Decker et al., Obstet Gynecol. 1982;60(4):481-487.
Dembo et al., Int J Rad Oncol Biol Phys. 1992;22(5):835-845.
Feld et al., J Clin Oncol. 1984;2(4):294-304.
Fontanesi et al., Am J Clin Oncol. 1993;16(5):412-417.
Gastrointestinal Tumor Study Group, Cancer. 1987;59(12):2006-2010.
Goetz et al., J Neurooncol. 2003;62(3):321-328.
Graves et al., Clin Cancer Res. 2003;9:3712-3721.
Harper et al., Semin Oncol. 2002;29(3 Suppl 8):3-6.
Antman et al., J Clin Oncol. 1993;11(7):1276-1285.
Johnson et al., J Clin Oncol. 1996;14(7):2054-2060.
Larson et al., Blood. 1995;85(8):2025-2037.
Miller et al., N Engl J Med. 1988;339(1):21-26.
Moertel, N Engl J Med. 1990;322(6):352-358.
Muggia et al., J Clin Oncol. 2000;18(1):106-115.
Murray et al., J Clin Oncol. 1993;11(2):336-344.
Nabholz et al., Clin Oncol. 2000;18(22):3758-3767.
Fisher et al., National Surgical Adjuvant Breast and Bowel Project B-23. J Clin Oncol. 2001;19(4):931-942.
Overgaard et al., N Engl J Med. 1997;337(14):949-955.
Overgaard et al., Lancet. 1999;353(9165):1641-1648.
Pastorino et al., J Clin Oncol. 1993;11(7):1216-1222.
Santoro et al., J Clin Oncol. 1995;13(7):1537-1545.
Selker et al., Neurosurgery. 2002;51(2):343-355.
Skarlos et al., Ann Oncol. 1994;5(7):601-607.
Thatcher et al., Lung Cancer. 1993;9(Suppl 1):s51-s67.
Trask et al., J Clin Oncol. 1991;9(7):1131-1137.

(Continued)

*Primary Examiner*—James D Anderson
(74) *Attorney, Agent, or Firm*—Darby & Darby P.C.

(57) ABSTRACT

The present invention relates to a method for treating non-melanotic cancers by administration of PABA. The present invention also relates to the potentiation of standard cancer treatment of radiation, radioimmunotherapy, and/or chemotherapy using PABA.

3 Claims, 10 Drawing Sheets

OTHER PUBLICATIONS

Trimble et al., J Clin Oncol. 1993;11(12):2405-2410.
Vergote, Cancer. 1992;69(3):741-749.
Wakai et al., Jpn J Cancer Res. 2000;91(12):1319-1325.
Whelan et al., J Natl Cancer Inst. 2002;94(15):1143-1150.
Wolmark et al., Clin Oncol. 1993;11(10):1879-1887.
Xiao et al., J Biochem. 2003;278:21767-21773.
Yu et al., Cancer Res. 2002;62:5743-5748.

* cited by examiner

Relative Abundance of CDC25A mRNA

FIGURE 9

G361 Melanoma

| PABA | − | + |
|---|---|---|
| G0/G1 | 77% | 27% |
| S | 12% | 72% |
| G2/M | 11% | 1% |

4T1 Breast Carcinoma

| PABA | − | + |
|---|---|---|
| G0/G1 | 65% | 43% |
| S | 10% | 40% |
| G2/M | 25% | 17% |

METHODS FOR TREATING NON-MELANOMA CANCERS WITH PABA

This application claims priority under 35 U.S.C. § 119(e) to U.S. provisional application No. 60/538,359, filed Jan. 21, 2004; the contents of which are hereby incorporated by reference in their entirety.

GOVERNMENT SUPPORT

This work was supported in part by DOD Grant No. OC010016 and NIH Grant No. ROICA91645. Pursuant to the terms of that grant, the federal government may have certain rights to this invention.

FIELD OF THE INVENTION

The present invention relates to the treatment of non-melanotic cancer using p-amino-benzoic acid (PABA). The invention also relates to the potentiation of existing cancer treatments such as radiation, radioimmunotherapy, chemotherapy, or a combination of radioimmunotherapy and chemotherapy with PABA.

BACKGROUND OF THE INVENTION

Cancer

Cancer accounts for nearly one-quarter of deaths in the United States, exceeded only by heart disease. In the year 2000, there were 553,091 cancer deaths in the US. In 2003, the American Cancer Society estimates that this number will increase to approximately 556,500, due to aging and growth of the population. Lung cancer is the most common fatal cancer in men (31%), followed by prostate cancer (10%), and colon & rectum cancer (10%). In women, lung (25%), breast (15%), and colon & rectum (11%) are the leading sites of cancer death. Among children, leukemia is the most common cancer among children ages 0-14 years and it comprises approximately 30% of all childhood cancers and accounts for the most childhood deaths. Acute lymphocytic cancer is the most common form of leukemia in children. It is estimated that 1.33 million new cases of cancer will be diagnosed in 2003 (American Cancer Society, 2003 Cancer Statistics Slide Set 2003).

In women, the incidence of breast cancer increases with age. 94% of new cases and 96% of deaths that were reported in the U.S. during 1996-2000 occurred in women who were 40 and over. It is estimated that more than 250,000 new cases of breast cancer will have been diagnosed in 2003, with approximate 200,000 diagnoses of invasive breast cancer. Among women in the United States, cancer of the ovary ranks fifth in incidence. There are no proven methods of prevention for ovarian cancer and it often is a rapidly fatal disease.

Current Treatments

Surgery, chemotherapy (CT) and radiation therapy (RT), and combinations thereof, remain the leading defenses against cancer, although recent advances in the field have led to widespread uses of specialized treatments such as angiogenesis inhibitors, biological therapies, including adjuvant therapy to boost the patient's immune system, antibody therapy, vaccine therapy, and photodynamic therapy. Radioimmunotherapy (RIT) is one such treatment which uses radioactively-conjugated monoclonal antibodies for both tumor localization by imaging, and for treatment. RIT is currently approved for the treatment of non-Hodgkin's lymphoma, and is being evaluated clinically for many tumor types, including malignant brain tumors.

However, CT and RT have numerous adverse effects. Patients undergoing CT may develop side effects including nausea, vomiting, diarrhea, hair loss, dry mouth and other oral complications, and cytopenia. For example, the main effect of paclitaxel (Taxol®) is red blood cell cytopenia due to effects on the bone marrow, however, it also causes allergic skin reactions, numbness in extremities, mouth sores, nausea, muscle and joint aches, vomiting, diarrhea, fatigue and hair loss. RT frequently causes anemia, skin irritation, temporary change in skin color in the treated area, temporary or permanent loss of hair in the area being treated, weight loss, fatigue, and hypoxic damage of normal tissue. Late toxic effects of radiation therapy, although uncommon, can include radiation pneumonitis, cardiac events, arm edema, brachial plexopathy, and the risk of second malignancies. Some chemotherapeutic drugs even have the very serious side effect of increasing the incidence of other types of cancer (Brown, Expert Opin Drug Saf. 2002; 1(3):253-67).

In addition to adverse effects of CT and RT, other limiting factors include development of drug resistance by the tumors, and induction of tumor cell growth arrest and senescence. While senescent tumors do not increase in size per se, they still retain the capacity to produce and secrete tumor stimulating mitogens and pro-angiogenic factors that can lead to tumor progression.

Accordingly, tumors continue to be difficult to treat with existing therapies. There is therefore a continued need in the art for non-toxic agents that can effect tumor cell killing and/or potentiate treatment with existing therapies, thereby allowing the use of lower effective doses of the toxic agents.

p-amino-benzoic-acid para-amino-benzoic acid (hereinafter "PABA"), is a water-soluble naturally-occurring compound that is essential for microorganisms and some animals, but not humans. PABA is a component of pteroylglutamate, a form of folic acid, and is a co-factor for B-complex vitamins. PABA also appears to function as a co-enzyme in the conversion of certain chemical intermediates to purines.

PABA is a common ingredient in sunscreens due to its capacity to absorb ultraviolet radiation. PABA has also been used in clinical trials for the treatment of connective tissue diseases (e.g., scleroderma, dermatomyositis) and in combination with salicylates for the treatment of rheumatic fever. U.S. Pat. No. 6,368,598 suggested the use of PABA as a non-essential part of a linking group in a drug complex for the treatment of prostate cancers. In this complex, PABA functions as a leaving group that is separated from the cytotoxic therapeutic portion of the drug complex by the action of enzymes present at the site of the intended therapeutic action. PABA also has been shown to inhibit cell cycle arrest and DNA repair. The present inventors have also previously discovered that PABA inhibits melanogenesis in vitro and in vivo, alone or in combination with chemotherapy or radiation therapy (RT) (see U.S. provisional patent application No. 60/436,394-filed Dec. 24, 2002, and U.S. application Ser. No. 10/746,206 filed Dec. 23, 2003). PABA was also unexpectedly shown to inhibit the in vitro proliferation of Lewis Lung carcinoma cells, suggesting a melanin-independent mechanism of action.

Since other agents that inhibit cell cycle arrest and DNA repair have been shown to increase the efficacy of chemotherapy (Yu et al., Cancer Res 2002; 62:5743-5748; and Xiao et al., J. Biochem 2003; 278:21767-21773), it was hypothesized that PABA would have a similar effect.

SUMMARY OF THE INVENTION

The present invention provides a method of treating non-melanotic cancer by administering to an individual an effective amount of PABA in combination with one or more of radiotherapy, chemotherapy, or radioimmunotherapy to patients in need thereof.

In a preferred embodiment, the PABA is administered in combination with chemotherapy (including angiogenesis inhibitors) and radioimmunotherapy.

In another embodiment, the PABA is administered with chemotherapy.

In yet another embodiment, the PABA is administered with radiotherapy, including external beam radiotherapy and brachytherapy.

In a further embodiment, the PABA is administered with radioimmunotherapy.

In one embodiment of the invention, the tumor is a non-Hodgkin's lymphoma and the PABA is administered in combination with monoclonal antibody $^{131}$I-tositumomab (BEXXAR®) or $^{90}$Y-rituxamab (ZEVALIN®).

In a preferred embodiment, the non-melanotic tumor is breast carcinoma, non-small cell lung carcinoma, ovarian carcinoma, pancreatic carcinoma, colon carcinoma, glioblastoma, or sarcoma.

The present invention also provides a method of potentiating the inhibition of non-melanotic tumor growth elicited by the administration of chemotherapy, radiotherapy or radioimmunotherapy, or a combination of two or more of such treatments by contacting the tumor cells with an effective amount of PABA.

In a preferred embodiment, PABA potentiates the effects of a combination of chemotherapy and radioimmunotherapy In another embodiment, PABA potentiates the effects of radiotherapy.

In still another embodiment, PABA potentiates the effects of chemotherapy.

In a further embodiment, PABA potentiates the effects of radioimmunotherapy.

In a preferred embodiment, the tumor is a breast carcinoma, a non-small cell lung carcinoma, an ovarian carcinoma, a pancreatic carcinoma, a colon carcinoma, a glioblastoma, a lymphoma, or a sarcoma.

In another embodiment, the present invention provides an oral dosage form comprising a non-melanotic cancer-treating effective amount of PABA and a pharmaceutically acceptable carrier.

The present invention provides a method for up-regulating the expression of c-Myc, CDC25A, Id-1, Id-2 or Id-3 in cancer cells by administering PABA to a subject suffering from a cancer.

The present invention further provides a method for down-regulating the expression of P21$^{CIP1}$, BRCA-2, H2A or H2B in cancer cells by administering PABA to a subject suffering from a cancer.

According to the present invention, a method is provided for promoting the accumulation of cancer cells in S-phase of the cell cycle by administering PABA to a subject suffering from a cancer.

Further, according to the present invention, a method is provided for promoting reactive oxygen species production in cancer cells by administering PABA to a subject suffering from cancer. In an embodiment of the present invention, a method is provided for promoting reactive oxygen species production by administering PABA and bortezomib.

BRIEF DESCRIPTION OF THE DRAWINGS

FIG. 1 demonstrates the effects of PABA, radiotherapy, and a combination of PABA and radiotherapy on the tumor growth of 4T1 breast carcinoma cells in vivo in chick embryos.

FIG. 2 demonstrates the effects of PABA, chemotherapy, and a combination of PABA and chemotherapy on the tumor growth of Lewis Lung carcinoma cells in vivo in chick embryos.

FIG. 3 demonstrates the effects of PABA, chemotherapy, and a combination of PABA and chemotherapy on the growth of 4T1 breast carcinoma cells in vivo in nude mice.

FIG. 5 demonstrates the effects of PABA, chemotherapy, and a combination of PABA and chemotherapy on the metastasis of 4T1 breast carcinoma cells to the lung in vivo in nude mice.

FIG. 6 demonstrates the response to PABA treatment of the proliferation of MCF-7 breast cancer cells treated with CT/RIT.

FIG. 7 demonstrates the response to PABA treatment of the proliferation of SKOV3 ovarian tumor cells treated with CT/RIT.

FIG. 8 demonstrates the increased expression of CDC25A mRNA in melanoma cells treated with PABA.

FIG. 9. FIG. 9 demonstrates the percentage of breast cancer cells and melanoma cells in the G0/G1, S and G2/M cell cycle phases following incubation in the presence or absence of PABA.

FIG. 10 demonstrates the increase in reactive oxygen species (ROS) in lung cancer cells following treatment with PABA. ROS was increased in PABA-treated cells relative to untreated controls. ROS was increased in cells treated with PABA and bortezomib relative to cells treated with bortezomib alone.

DETAILED DESCRIPTION

Figure 1:
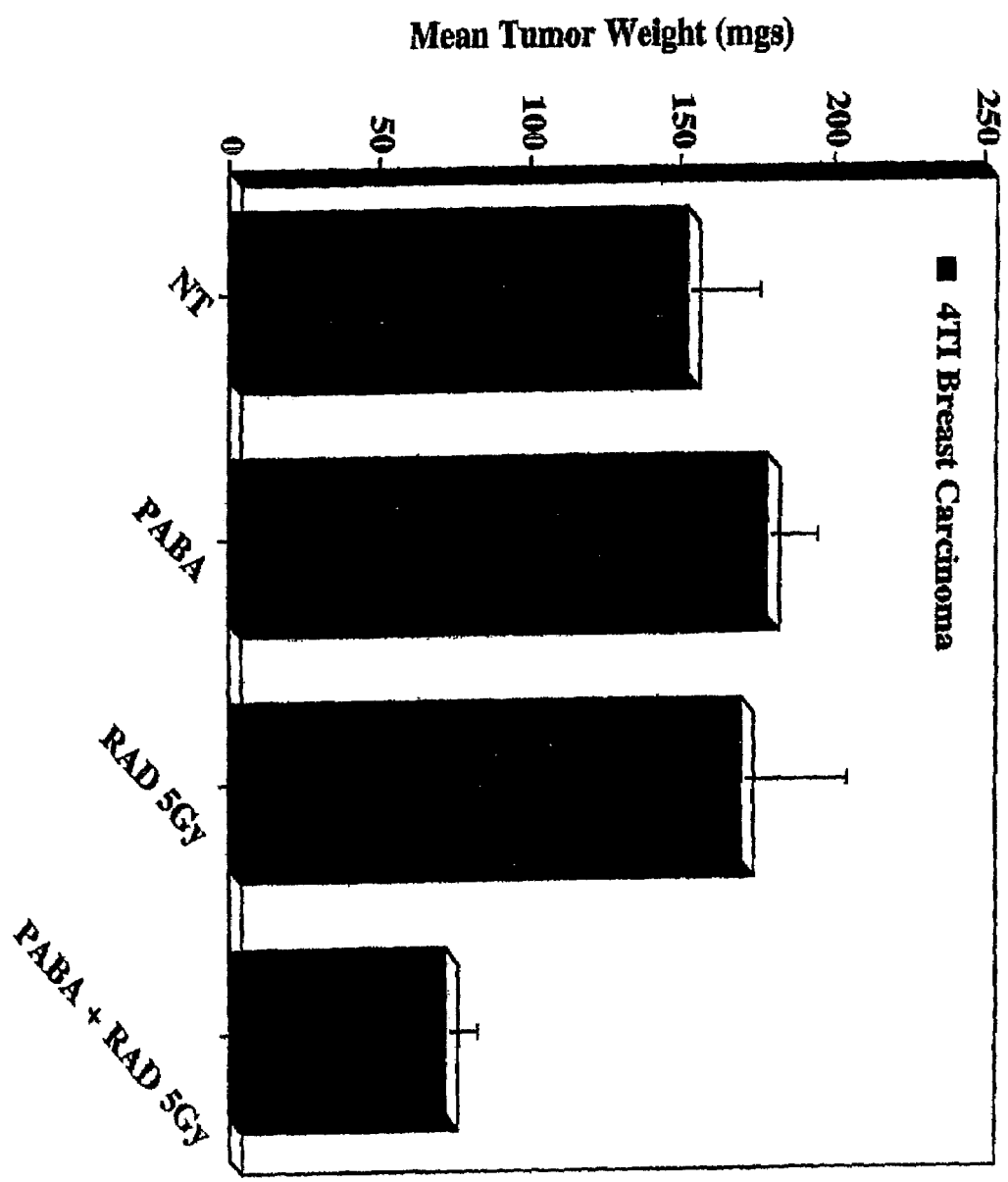
FIG. 1.

It has now been surprisingly discovered that PABA can reduce the proliferation of non-melanotic cancer including hormone-dependent metastatic breast and ovarian carcinoma cells, and can potentiate growth inhibition of these tumors treated with RIT, CT, and combination RIT/CT. This is surprising because PABA inhibits melanogenesis, which is implicated in the malignant conversion of melanocytes to melanoma but melanogenesis is not expressed in other cell types. Potentiation of tumor growth inhibition with PABA will permit the use of lower (e.g., sub-optimal or sub-threshold), less toxic, effective doses of RIT, CT or RIT/CT for numerous tumor types, thereby mitigating adverse effects of therapy. PABA administration can also protect normal cells, thereby leading to an overall improvement in the effectiveness of the treatment regimen, i.e., improve the therapeutic index.

Definitions

"para-amino-benzoic-acid" (PABA) is commercially available from, e.g., Sigma-Aldrich Chemical Co., St. Louis, Mo.

"Cancer" refers to abnormal, malignant proliferations of cells originating from epithelial cell tissue (carcinomas), blood cells (leukemias, lymphomas, myelomas), connective tissue (sarcomas), or glial or supportive cells (gliomas). In one embodiment, the invention relates to the treatment of carcinomas and blood cell malignancies. In a preferred embodiment, the invention relates to the treatment of lung tumors, breast tumors, ovarian tumors, pancreatic tumors, glioblastoma tumors, and sarcomas.

The term cancer includes but is not limited to the following: acute lymphoblastic leukemia, acute myeloid leukemia, adrenocortical carcinoma, carcinoma, aids-related cancers, aids-related lymphoma, anal cancer, astrocytoma (cerebellar), bile duct cancer (extrahepatic), bladder cancer, bone cancer (osteosarcoma/malignant fibrous histiocytoma), brain stem glioma, ependymoma, childhood visual pathway and hypothalamic glioma, breast cancer (including male), bronchial adenomas/carcinoids, carcinoid tumor (gastrointestinal), islet cell carcinoma, carcinoma of unknown primary origin, central nervous system lymphoma, cervical cancer, childhood cancers, chronic lymphocytic leukemia, chronic myelogenous leukemia, chronic myeloproliferative disorders, clear cell sarcoma of tendon sheaths, colon cancer, colorectal cancer, cutaneous t-cell lymphoma, endometrial cancer, ependymoma, ovarian epithelial cancer, esophageal cancer, Ewing's family of tumors, extracranial germ cell tumor, extragonadal germ cell tumor, intraocular melanoma, retinoblastoma, gallbladder cancer, gastric (stomach) cancer, germ cell tumor, ovarian germ cell tumor, gestational trophoblastic tumor, hairy cell leukemia, head and neck cancer, hepatocellular (liver) cancer, Hodgkin's lymphoma, hypopharyngeal cancer, Kaposi's sarcoma, kidney cancer, laryngeal cancer, lip and oral cavity cancer, liver cancer, lung cancer (non-small cell and small cell), lymphoma, macroglobulinemia, Waldenström's, malignant mesothelioma, medulloblastoma, Merkel cell carcinoma, metastatic squamous neck cancer with occult primary, multiple endocrine neoplasia syndrome, multiple myeloma/plasma cell neoplasm, mycosis fungoides, myelodysplastic syndromes, myelodysplastic/myeloproliferative diseases, multiple myeloma, chronic myeloproliferative disorders, nasal cavity and paranasal sinus cancer, nasopharyngeal cancer, neuroblastoma, oral cancer, oral cavity and lip cancer, oropharyngeal cancer, ovarian low malignant potential tumor, pancreatic cancer, paranasal sinus and nasal cavity cancer, parathyroid cancer, penile cancer, pheochromocytoma, pineal and supratentorial primitive neuroectodermal tumors, pituitary tumor, pleuropulmonary blastoma, prostate cancer, rectal cancer, renal cell (kidney) cancer, renal pelvis and ureter, transitional cell cancer, rhabdomyosarcoma, salivary gland cancer, soft tissue sarcoma, Sezary syndrome, skin cancer (non-melanotic), small intestine cancer, supratentorial primitive neuroectodermal tumors, T-cell lymphoma, cutaneous testicular cancer, thymoma, thymic carcinoma, thyroid cancer, urethral cancer, endometrial uterine cancer, uterine sarcoma, vaginal cancer, vulvar cancer, and Wilm's tumor.

The term "radiation therapy" or "radiotherapy" refers to use of high-energy radiation to treat cancer. Radiation therapy includes externally administered radiation, e.g., external beam radiation therapy from a linear accelerator, and brachytherapy, in which the source of irradiation is placed close to the surface of the body or within a body cavity. Common radioisotopes used include but are not limited to cesium ($^{137}$Cs), cobalt ($^{60}$Co), iodine ($^{131}$I), phosphorus-32 ($^{32}$P), gold-198 ($^{198}$Au), iridium-192 ($^{192}$Ir), yttrium-90 ($^{90}$Y), and palladium-109 ($^{109}$Pd). Radiation is generally measured in Gray units (Gy), where 1 Gy=100 rads.

As used herein, the term "radioimmunotherapy" (RIT) refers to localized delivery of ionizing radiation coupled to a monoclonal antibody (mAb) or other suitable radiation delivery vehicles (i.e., peptides, organic compounds, stem cells, etc.). The radiolabeled mAb is administered in to the blood circulation and localizes to the surface of tumor cells for which the mAb is specific. The present invention encompasses all radioisotopes suitable for use in RIT, including beta-, alpha-, and gamma-emitting isotopes, which include, but are not limited to, beta-emitters yttrium-90 ($^{90}$Y), copper-67 ($^{67}$Cu), gamma-emitting iodine-131 ($^{131}$I) and Rhenium-186 ($^{186}$Re), and alpha-emitters bismuth-213 ($^{213}$Bi), terbium-149 ($^{149}$Tb) and actinium-225 ($^{225}$At). Alpha-emitters are well suited for targeting micrometastatic disease and single-tumor cells such as leukemia and other blood-borne disease.

"Chemotherapy" (CT) refers to treatment with anti-cancer drugs. The term encompasses numerous classes of agents including platinum-based drugs, alkylating agents, anti-metabolites, anti-miotic agents, anti-microtubule agents, plant alkaloids, anti-tumor antibiotics, anti-angiogenic agents, kinase inhibitors, proteasome inhibitors, EGER inhibitors, HER dimerization inhibitors, VEGE inhibitors, antisense molecules, and includes antibodies. Such drugs include but are not limited to adriamycin, melphalan, ara-C, BiCNU, busulfan, CCNU, pentostatin, the platinum-based drugs carboplatin, cisplatin and oxaliplatin, cyclophosphamide, daunorubicin, epirubicin, dacarbazine, 5-fluorouracil (5-FU), fludarabine, hydroxyurea, idarubicin, ifosfamide, methotrexate, altretamine, mithramycin, mitomycin, bleomycin, chlorambucil, mitoxantrone, nitrogen mustard, mercaptopurine, mitozantrone, paclitaxel (TAXOL®), vinblastine, vincristine, vindesine, etoposide, gemcitabine, monoclonal antibodies such as HERCEPTIN®, RITUXAN®, CAMPATH®, ZEVELIN® and BEXXAR®, irinotecan, leustatin, vinorelbine, STI-571 (GLEEVAC®), tamoxifen, docetaxel, topotecan, capecetabine (XELODA®), raltitrexed, streptozocin, tegafur with uracil, temozolomide, thioguanine, thiotepa, podophyllotoxin, filgristim, profimer sodium, letrozole, amifostine, anastrozole, temozolomide, arsenic trioxide, epithalones A and B tretinioin, interleukins (e.g., 2 and 12) and interferons, e.g., alpha and gamma. Antiangiogenic agents include but are not limited to BMS-275291, Dalteparin (FRAGMIN®) 2-methoxyestradiol (2-ME), thalodmide, CC-5013 (thalidomide analog), maspin, combretastatin A4 phosphate, LY317615, soy isoflavone (genistein; soy protein isolate), AE-941 (NEOVASTAT™; GW786034), anti-VEGF antibody (Bevacizumab; AVASTIN™), PTK787/ZK 222584, VEGF-trap, ZD6474, EMD 121974, anti-anb3 integrin antibody (Medi-522; VITAXIN™), carboxyamidotriazole (CAI), celecoxib (CELEBREX®), halofuginone hydrobromide (TEMPOSTATIN™), and Rofecoxib (VIOXX®). Other agents include bortezomib, huBr-E3, GENASENSE, GANITE, FIT-3 ligand, MLN591RL, MLN27904, MLN576 and MLN518.

The term "chemotherapy" also includes gene therapy with agents such as interferon and the interleukins, i.e., administration of a vector encoding genes for the interferons or interleukins. See e.g., Heller et al., Technol Cancer Res Treat. 2002; 1(3):205-9.

As used herein, the terms "treatment" or "treat" mean the lessening or ameliorating of at least one abnormal or undesirable condition associated with cancer. Treatment may, for example, cause a reduction in the rate or amount of growth of a tumor. Treatment also includes reducing or ameliorating the undesirable symptoms of cancer. The term "treat" also denotes prevention or delay of the patients presenting with additional symptoms associated with cancer. The foregoing are merely non-limiting examples of the treatment of cancer.

As used herein, a "therapeutically effective amount" of an agent is an amount sufficient to ameliorate at least one symptom, behavior or event, associated with a pathological, abnormal or otherwise undesirable condition, e.g., cancer, or an amount sufficient to prevent or lessen the probability that such a condition will occur or re-occur, or an amount sufficient to delay worsening of such a condition. In one embodiment, the term "therapeutically effective amount" is used to refer to an amount having antiproliferative effect on tumor cells.

Preferably, the therapeutically effective amount has apoptotic or anti-proliferative activity, or is capable of inducing cell death, and preferably death of benign or malignant tumor cells, in particular cancer cells. Efficacy can be measured in conventional ways, depending on the condition to be treated. For cancer therapy, efficacy can, for example, be measured by assessing the time for disease progression, or determining the response rates. In a preferred embodiment, an effective amount of PABA is an amount that reduces or inhibits the growth and/or proliferation of tumor cells in an individual in need of treatment alone, or in combination with CT, RT, RIT, or RIT/CT.

As used herein, the phrase "individual or mammal in need of such treatment" refers to a mammal suffering from at least one type of hyperproliferative disorder or who has been diagnosed with cancer.

The phrase "in combination" or "in combination with" refers to a method of treatment in which two or more treatments are administered collectively or according to a specific sequence, such that they produce a desirable effect.

The term "potentiate" means to increase the effect of, or act synergistically with, a drug or a biologic. In another embodiment, the term potentiate means that sub-optimal or sub-threshold amounts of individual CT, RIT or CT/RIT agents can be administered in combination with PABA and still render a therapeutic effect. In one embodiment of the present invention, PABA potentiates the tumorcidal activity or inhibition of tumor growth effected by RIT or RIT/CT.

The term "sub-threshold" refers to an amount of an active ingredient that is inadequate to produce a response, i.e., an amount below the minimum effective amount when the active ingredient is used as monotherapy.

The term "sub-optimal" means an amount of an active ingredient that produces a response but not to its full extent, which would be achieved with a higher amount.

The phrase "pharmaceutically acceptable" refers to molecular entities and compositions that are physiologically tolerable and do not typically produce an allergic or similar toxicity (for example, gastric upset, dizziness and the like) when administered to an individual. Preferably, and particularly where a formulation is used in humans, the term "pharmaceutically acceptable" may mean approved by a regulatory agency (for example, the U.S. Food and Drug Agency) or listed in a generally recognized pharmacopeia for use in animals (e.g., the U.S. Pharmacopeia).

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

Formulations

Formulations. For use in the present invention, PABA may be formulated into a pharmaceutical composition. The pharmaceutical composition may include additives, such as a pharmaceutically acceptable carrier or diluent, a flavorant, a sweetener, a preservative, a dye, a binder, a suspending agent, a dispersing agent, a colorant, a disintegrant, an excipient, a film forming agent, a lubricant, a plasticizer, an edible oil or any combination of two or more of the foregoing.

Suitable pharmaceutically acceptable carriers or diluents include, but are not limited to, ethanol, water, glycerol, propylene glycol, aloe vera gel, allantoin, glycerin, vitamin A and E oils, mineral oil, PPG2 myristyl propionate, magnesium carbonate, potassium phosphate, vegetable oil, animal oil, and solketal. Preferred carriers are vegetable and mineral oils.

Suitable binders include, but are not limited to, starch, gelatin, natural sugars, such as glucose, sucrose and lactose; corn sweeteners, natural and synthetic gums, such as acacia, tragacanth, vegetable gum, and sodium alginate, carboxymethylcellulose, hydroxypropylmethylcellulose, polyethylene glycol, povidone, waxes; and the like.

Suitable disintegrants include, but are not limited to, starch, e.g., corn starch, methyl cellulose, agar, bentonite, xanthan gum, sodium starch glycolate, crosspovidone and the like.

Suitable lubricants include, but are not limited to, sodium oleate, sodium stearate, sodium stearyl fumarate, magnesium stearate, sodium benzoate, sodium acetate, sodium chloride and the like.

A suitable suspending agent is, but is not limited to, bentonite, ethoxylated isostearyl alcohols, polyoxyethylene sorbitol and sorbitan esters, microcrystalline cellulose, aluminum metahydroxide, agar-agar and tragacanth, or mixtures of two or more of these substances, and the like.

Suitable dispersing and suspending agents include, but are not limited to, synthetic and natural gums, such as vegetable gum, tragacanth, acacia, alginate, dextran, sodium carboxymethylcellulose, methylcellulose, polyvinyl-pyrrolidone and gelatin.

Suitable film forming agents include, but are not limited to, hydroxypropylmethylcellulose, ethylcellulose and polymethacrylates.

Suitable plasticizers include, but are not limited to, polyethylene glycols of different molecular weights (e.g., 200-8000 Da) and propylene glycol.

Suitable colorants include, but are not limited to, ferric oxide(s), titanium dioxide and natural and synthetic lakes.

Suitable edible oils include, but are not limited to, cottonseed oil, sesame oil, coconut oil and peanut oil.

Examples of additional additives include, but are not limited to, sorbitol, talc, stearic acid, dicalcium phosphate and polydextrose.

Dosages and Dosage Forms

Dosages. The pharmaceutical composition or unit dosage form of the present invention, i.e., PABA, may be administered according to a dosage and administration regimen defined by routine testing in order to obtain optimal (or sub-optimal or sub-threshold) activity while minimizing toxicity or side-effects for a particular patient. Typically, dosages will determined by those skilled in the art on a case-by-case basis, depending upon the tumor type, stage, location, and prognosis of the individual, and other factors such as weight, sex and age of the individual, the particular dosage form employed, and the route of administration utilized. Pharmacokinetics and pharmacodynamics such as half-life ($t_{1/2}$), peak plasma concentration ($c_{max}$), time to peak plasma concentration ($t_{max}$), and exposure as measured by area under the curve (AUC) can be obtained using ordinary methods known in the art.

Data obtained from cell culture assay or animal studies may be used to formulate a therapeutic dosage range for use in humans and non-human animals. The dosage of compounds used in therapeutic methods of the present invention preferably lie within a range of circulating concentrations that includes the $ED_{50}$ concentration (effective for 50% of the tested population) but with little or no toxicity.

A therapeutically effective dose may be initially estimated from cell culture assays and formulated in animal models to achieve a circulating concentration range that includes the $IC_{50}$. The $IC_{50}$ concentration of a compound is the concentration that achieves a half-maximal inhibition of symptoms and can be determined by, e.g., cell culture assays. Appropriate dosages for use in a particular individual, for example in human patients, may then be more accurately determined using such information.

PABA has a mean half life of about 0.5 hours with a peak plasma concentration occurring about ¾ of an hour after ingestion.

In one embodiment, PABA may be administered, alone or in combination with CT, RT and/or CT/RIT in the range of 10 mg/day to 20 g/day of PABA. Preferably, PABA is administered in an amount in a range from about 20 mg/day to about 12 g/day, more preferably in a range from about 500 mg/day to about 8 g/day.

Radiation therapy is typically administered in doses of 1 cGy to 100 Gy. Often, radiation therapy is administered in doses of 2 cGy to 20 Gy. Factors such as dose rate delivered, tumor size, and radiosensitivity play a major role in determining therapeutic response, while target-to-nontarget ratios and, particularly, circulating radioactivity to the bone marrow determine the major dose-limiting toxicities.

Dosages of chemotherapy are not only drug-type specific, but also depend to a large extent on the individual patient, the tumor-type, and the stage of the disease, and accordingly, are determined by one of ordinary skill in the art. By way of example, standard doses of paclitaxel in combination with carboplatin for ovarian and lung cancer are 175 mg/m² of the former and AUC 5 mg/ml *min of the latter.

For RIT, standard doses are typically in a range from about 0.5-2.5 mg/ml antibody and about 0.3-0.4 mCi/kg isotope.

Unit dosage forms. The above compositions of PABA may be formulated as unit dosage forms such as tablets, pills, capsules, caplets, boluses, powders, granules, sterile parenteral solutions, sterile parenteral suspensions, sterile parenteral emulsions, elixirs, tinctures, metered aerosol or liquid sprays, drops, ampoules, autoinjector devices or suppositories. Unit dosage forms may be used for oral, parenteral, intranasal, sublingual or rectal administration, or for administration by inhalation or insufflation, transdermal patches, and a lyophilized composition. In general, any mode of delivery of active ingredients that results in their systemic availability can be used.

Preferably the unit dosage form of PABA is an oral dosage form, most preferably a solid oral dosage form. Thus, preferred dosage forms include tablets, pills, caplets and capsules. PABA-containing solutions and suspensions for oral administration are also preferred. However, PABA can also be formulated for parenteral administration. Parenteral preparations (e.g., injectable preparations in saline and preparations for powder jet systems) are preferred for CT and RIT.

Solid unit dosage forms can be prepared by mixing an active agent of the present invention with a pharmaceutically acceptable carrier and any other desired additives, e.g., excipients, fillers, as described above. The mixture is typically mixed until a homogeneous mixture of the active agents of the present invention and the carrier and any other desired additives is formed, i.e., until the active agent is dispersed evenly throughout the composition. In this case, the compositions can be formed as dry or moist granules.

Dosage forms with predetermined amounts of PABA may be formulated starting with compositions with known quantities of PABA using methods well known in the art. In a preferred embodiment a dosage form is obtained by mixing compositions comprising known quantities of PABA.

Dosage forms can be formulated as, for example, "immediate release" dosage forms. "Immediate release" dosage forms are typically formulated as tablets that release at least 70%-90% of the active ingredient within 30-60 min when tested in a drug dissolution test, e.g., U.S. Pharmacopeia standard <711>. In a preferred embodiment, immediate dosage forms release 75% of active ingredients in 45 min.

Dosage forms can also be formulated as, for example, "controlled release" dosage forms. "Controlled," "sustained," "extended" or "time release" dosage forms are equivalent terms that describe the type of active agent delivery that occurs when the active agent is released from a delivery vehicle at an ascertainable and modifiable rate over a period of time, which is generally on the order of minutes, hours or days, typically ranging from about sixty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract. Typical parameters for dissolution test of controlled release forms are found in U.S. Pharmacopeia standard <724>.

Dosage forms can also be formulated to deliver active agent in multiphasic stages whereby a first fraction of an active ingredient is released at a first rate and at least a second fraction of active ingredient is released at a second rate. In a preferred embodiment, a dosage form can be formulated to deliver active agent in a biphasic manner, comprising a first "immediate release phase", wherein a fraction of active ingredient is delivered at a rate set forth above for immediate release dosage forms, and a second "controlled release phase," wherein the remainder of the active ingredient is released in a controlled release manner, as set forth above for controlled release dosage forms.

Tablets or pills can be coated or otherwise compounded to form a unit dosage form which has delayed and/or prolonged action, such as time release and controlled release unit dosage forms. For example, the tablet or pill can comprise an inner or core dosage and an outer dosage component, the latter being in the form of a layer or envelope over the former. The two components can be separated by an enteric layer which serves to resist disintegration in the stomach and permits the inner component to pass intact into the duodenum or to be delayed in release. Enteric coatings include but are not limited to cellulose acetate phthalate, hydroxy propyl methyl cellulose phthalate, and methacrylic acid copolymers.

Biodegradable polymers for controlling the release of the active agents, include, but are not limited to, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

For liquid dosage forms, the active substances or their physiologically acceptable salts are brought into solution, suspension or emulsion, optionally with the usually employed substances such as solubilizers, emulsifiers or other auxiliaries. Solvents for the active combinations and the corresponding physiologically acceptable salts, can include water, physiological salt solutions or alcohols, e.g. ethanol, propane-diol or glycerol. Additionally, sugar solutions such as glucose or mannitol solutions may be used. A mixture of the various solvents mentioned may further be used in the present invention.

A transdermal dosage form of e.g., PABA, also is contemplated by the present invention. Transdermal forms may be a diffusion-driven transdermal system (transdermal patch) using either a fluid reservoir or a drug-in-adhesive matrix system. Other transdermal dosage forms include, but are not limited to, topical gels, lotions, ointments, transmucosal systems and devices, and iontohoretic (electrical diffusion) delivery system. Transdermal dosage forms may be used for timed release and controlled release of the active agents of the present invention.

Pharmaceutical compositions and unit dosage forms of the present invention for administration parenterally, and in particular by injection, typically include a pharmaceutically acceptable carrier, as described above. A preferred liquid carrier is vegetable oil. Injection may be, for example, intravenous, intrathecal, intramuscular, intratracheal, or subcutaneous.

The active agent also can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active agent of the present invention also may be coupled with soluble polymers as targetable drug carriers. Such polymers include, but are not limited to, polyvinylpyrrolidone, pyran copolymer, polyhydroxypropyl-methacryl-amidephenol, polyhydroxy-ethylaspartamidephenol, and polyethyl-eneoxideopolylysine substituted with palmitoyl residues.

Administration

The pharmaceutical composition or unit dosage forms of the present invention may be administered to a mammal, preferably a human being, in need of cancer or other hypoproliferative disorder treatment.

The pharmaceutical formulations or unit dosage forms of the present invention may be administered by a variety of routes including for example, intravenous, intratracheal, subcutaneous, oral, intratumoral, mucosal parenteral, buccal, rectal, sublingual, ophthalmic, pulmonary, transmucosal, transdermal, and intramuscular. Unit dosage forms also can be administered in intranasal form via topical use of suitable intranasal vehicles, or via transdermal routes, using those forms of transdermal skin patches known to those of ordinary skill in the art. Oral or parenteral administration is preferred. Also preferred is administration by local intratumoral injection.

The pharmaceutical composition or unit dosage form may be administered in a single daily dose, or the total daily dosage may be administered in divided doses. The combination of PABA with RT, CT or RIT/CT may be co-administered simultaneously or sequentially administered. Thus, according to the present invention, PABA can be administered prior to or following RT, CT, RIT or a combination thereof. Further, according to the present invention, PABA can be administered simultaneously with RT, CT, RIT or a combination thereof. The compounds (i.e., PABA and a chemotherapeutic agent) can be administered together in one dosage form or in separate dosage forms. The compounds preferably will be provided as separate dosage forms.

The exact dosage and administration regimen utilizing the combination therapy of the present invention is selected in accordance with a variety of factors including type, species, age, weight, sex and medical condition of the patient; the route of administration; the renal and hepatic function of the patient; the treatment history of the patient; and the responsiveness of the patient. Optimal precision in achieving concentrations of compounds within the range that yields efficacy without toxicity requires a regimen based on the kinetics of the drug's availability to target sites. This involves a consideration of the absorption, distribution, metabolism, excretion of a drug, and responsiveness of the patient to the dosage regimen. However, such fine tuning of the therapeutic regimen is routine in light of the guidelines given herein.

EXAMPLES

The present invention is further described by means of the examples, presented below. The use of such examples is illustrative only and in no way limits the scope and meaning of the invention or of any exemplified term. Likewise, the invention is not limited to any particular preferred embodiment described herein. Indeed, many modifications and variations of the invention will be apparent to those skilled in the art upon reading this specification and can be made without departing from its spirit and scope.

Example 1

Effects of PABA on Tumor Radio- and Chemo-sensitivity in Chick Embryo Tumor Growth Models Methods Lewis Lung carcinoma cells and murine 4T1 breast carcinoma cells (available from American Type Culture Collection, Rockville, MD-No. CRL-2539), were cultured in growth medium in the presence or absence of PABA (100 ug/ml) for at least 7 days. The cells were harvested, washed and resuspended in sterile PBS, followed by implantation on the chorioallantoic membranes (CAM) of 10-day old chick embryos. Embryos were allowed to incubate for 24 hours. The embryos were then treated with either a single fraction dose of ionizing radiation (5.0 Gy) or TAXOL® (0.01 µM)

and allowed to incubate for 7 days. Tumor growth was assessed by measuring the wet weights of resected tumors (5-10 tumors per condition).

Results

Figure 2:
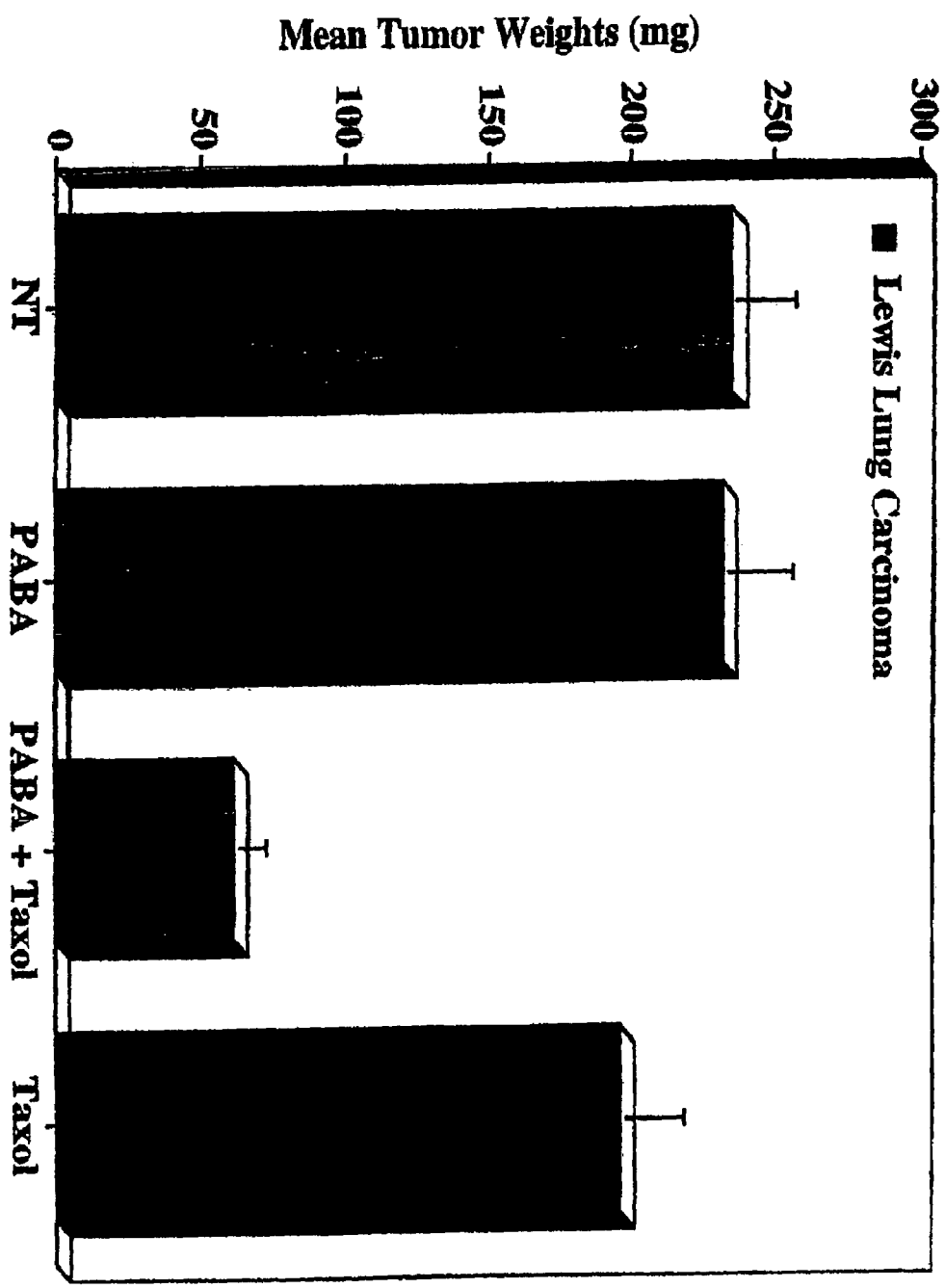
FIG. 2.

Neither PABA alone nor a single fraction dose of ionizing radiation had any effect on murine 4T1 breast carcinoma tumor growth. By contrast, a combination of PABA and radiation inhibited tumor growth by approximately 65-70% (FIG. 1). Similarly, neither PABA nor TAXOL® alone inhibited the growth of Lewis Lung tumors, while the combination of and PABA and TAXOL® inhibited tumor growth by approximately 75% compared to untreated controls or single-agent treatment (FIG. 2).

Example 2

Effects of PABA on Breast Tumor Radio- and Chemosensitivity in Mouse Tumor Growth Models Methods Sub-confluent cultures of 4T1 breast carcinoma cells were harvested, washed and resuspended in PBS. Female nude mice or Balb/c strain mice were injected subcutaneously with approximately $1 \times 10^6$ tumor cells. Subcutaneous tumors were allowed to grow for 7 days, at which time the mice were treated daily by intraperitoneal injections of the following:

PABA alone (500 µg/mouse)
Radiation alone (9.0 Gy)
PABA and radiation
Docetaxel (8.0 mg/kg 1 time/week, intraperitoneal administration)
PABA and docetaxel (daily PABA and intraperitoneal administration of 8.0 mg/kg docetaxel 1 time/week)

Untreated mice were used as a control. Tumor growth was gauged by weekly caliper measurements. After 28 days, the mice were sacrificed and tumor volumes were calculated by standard methods using the formula V+L×W/2, where V=volume, L=length and W=width.

Results

Figure 4:
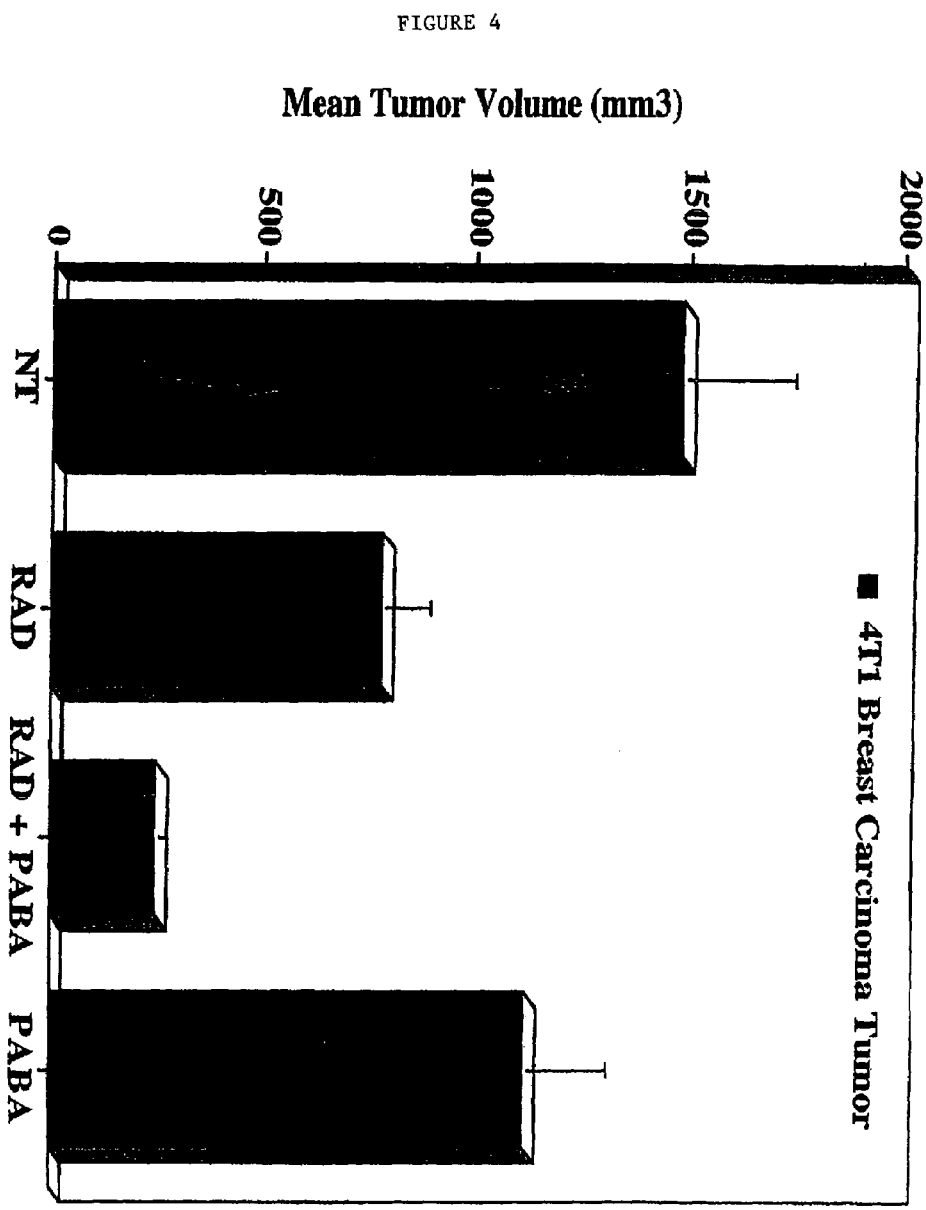
FIG. 4 demonstrates the effect of a combination of PABA and radiotherapy in nude mice.

FIG. 4 demonstrates that, compared to untreated control mice, treatment with radiation alone reduced mean tumor volume (in $mm^3$) by about 50%; treatment with PABA alone reduced tumor volume by about 26%; and the combination of PABA and radiation reduced tumor volume by about 83%, or about 6 times lower than untreated controls.

Figure 3:
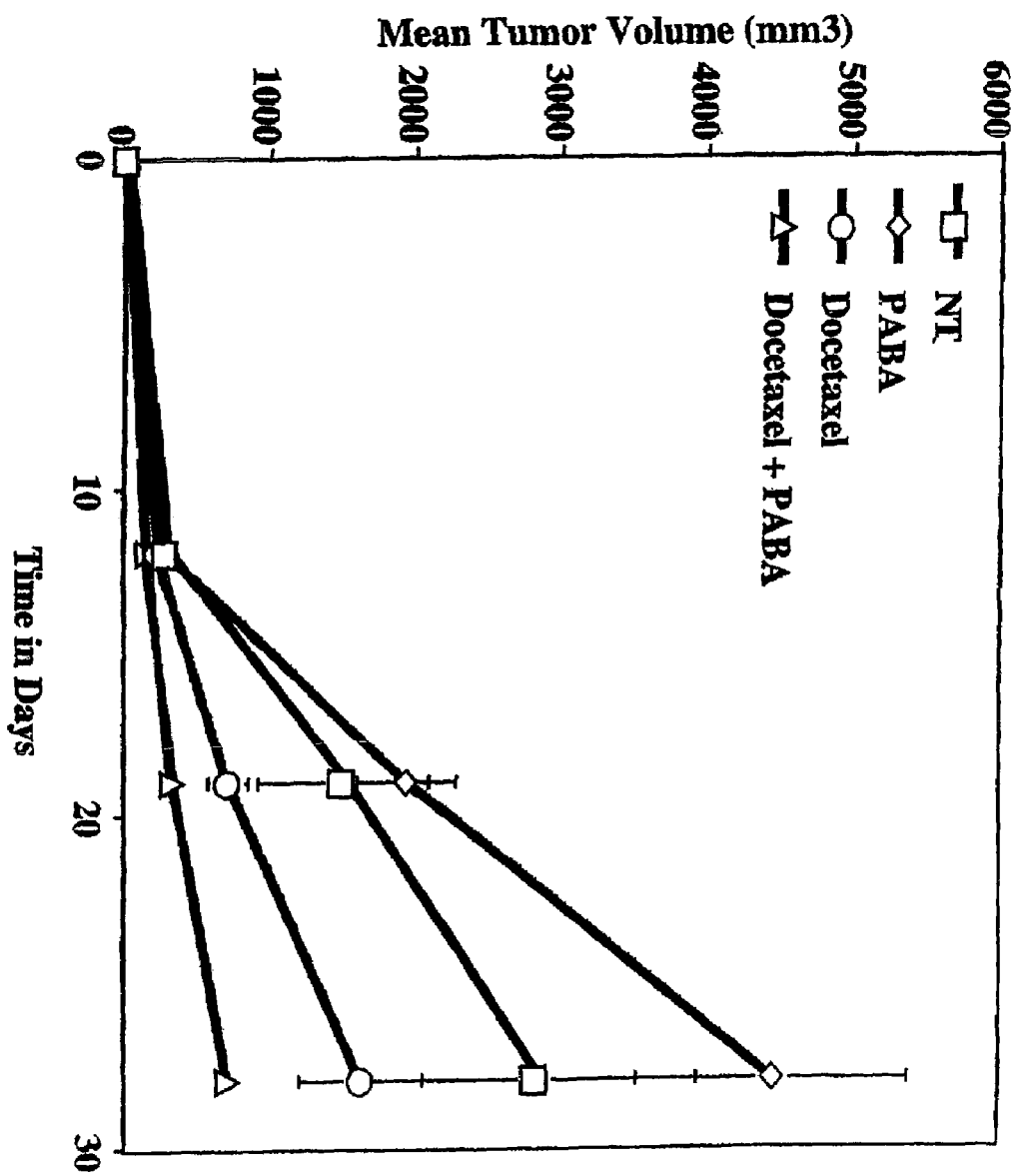
FIG. 3.
Figure 5:
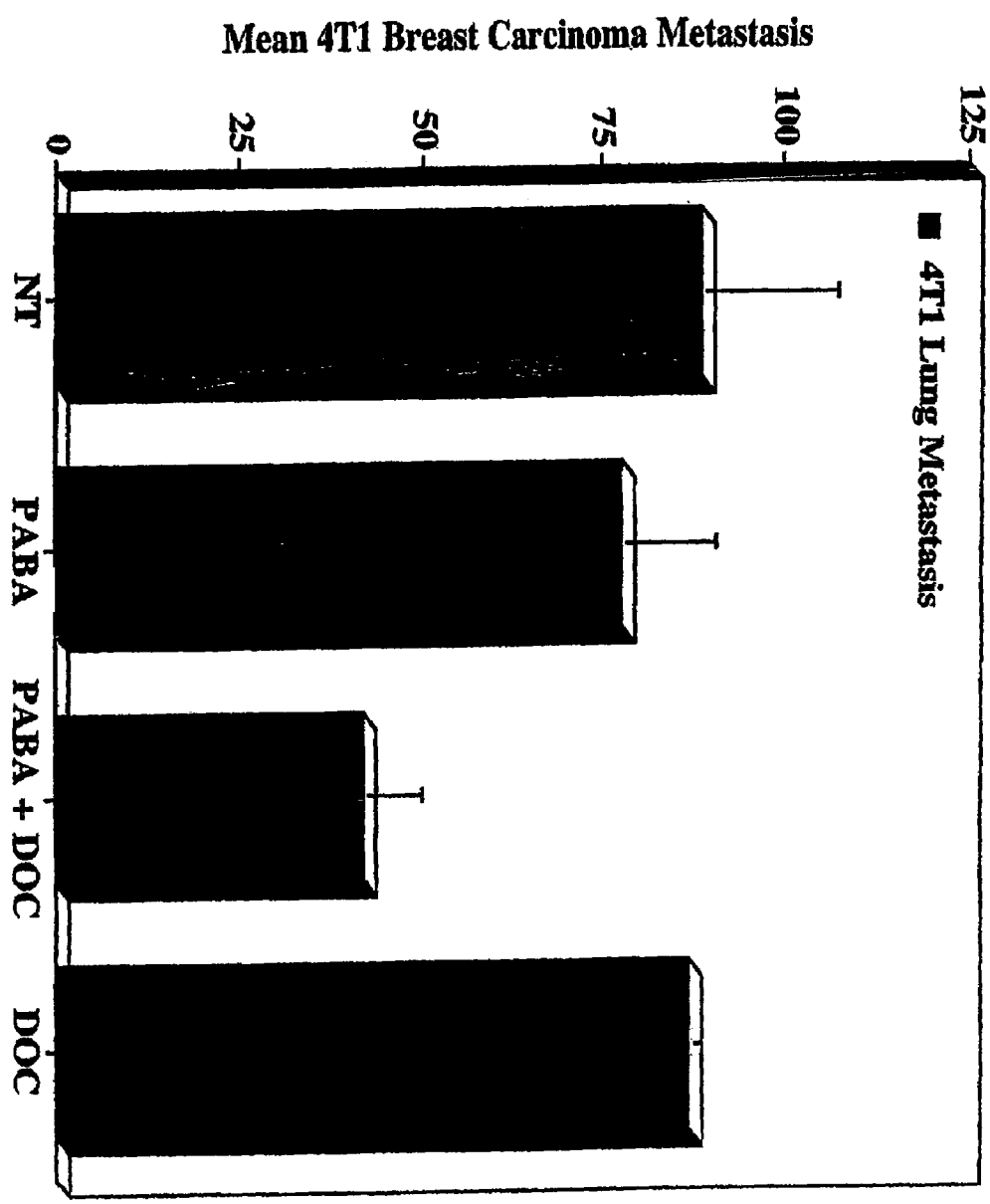
FIG. 5.

Treatment with docetaxel alone resulted in about a 45% reduction of tumor growth while the combination of docetaxel and PABA resulted in about an 80% reduction in tumor growth (FIG. 3). Unexpectedly, treatment with PABA and docetaxel also inhibited metastasis of the 4T1 cells to the lungs (FIG. 5).

Example 3

Metastatic Breast Cancer Treatment in Humans with a Combination of TAXOL® and PABA Treatment A woman with metastatic breast cancer who had been treated with, and progressed, with gemeitabine (GEMZAR®), and who had previously received a course of docetaxel (TAXOTERE®), underwent a treatment regiment comprising weekly TAXOL® (30 mg/m²) in combination with oral PABA at 6 mg/day. Progress was measured by evaluation of two sets of breast cancer-associated serum markers, carcinogenic embryonic antigen (CEA) and cancer antigen 27-29 (CA27-29), which, prior to treatment were as follows: CEA=618.4 and CA27-29=314.3.

Results

After 15 days, CEA dropped to 493 and CA27-29 dropped to 314. Other symptoms improved, including amelioration of the patients' shortness of breath (resulting from lung metastasis). After one more month of treatment, CEA dropped to 368.9 and CA27-29 to 291.2.

These results were surprising and unexpected given the patients' prior treatment with docetaxel, a microtubule inhibitor with a similar mechanism of action to TAXOL® (paclitaxel).

Example 4

Human Non-Small Cell Lung Cancer Treatment with NAVELBINE® (Vinorelbine), GEMZAR® (Gemcitabine) and PABA Treatment A 48 year-old woman presented with non-small cell lung cancer, and with extensive mediastinal disease and bilateral supra clavicular adenopathy. She had previously failed treatment with docetaxel and cisplatin, and also failed treatment with IRESSA® (gefitinib). Following a 7-day pre-load with PABA alone (at 8 g QID), she underwent weekly chemotherapy with a combination regimen of NAVELBINE®, GEMZAR®, and PABA. The regimen consisted for 3 weeks on and 1 week off, and 3 cycles were competed over a period of 12 weeks.

Results

Following treatment, a CT scan demonstrated a reduction in the mediastinal mass, and improved air entry into the lung, as well as a reduction in the mass in the lymph nodes at the back of the neck. Improvements in breathing, shortness of breath, and chest pain were also observed, permitting discontinuation of supportive pain medications.

Example 5

Effects of PABA, Chemotherapy, and Radioimmunotherapy on the Proliferation of Breast and Ovarian Tumor Cells Methods Pharmaceutical grade $^{90}Y$ was buffered in 0.05M acetate and incubated with MX-DTPA-huBrE-3 and 5 mM EDTA for 1 hr, followed by purification on a Bio-Gel P6 column eluted with 1% human serum albumin to generate radiolabeled $^{90}Y$-huBrE-3 antibody. MCF7 breast carcinoma cells were incubated with and without PABA (0.1 mg/ml) in DMEM media for 3 days, and then exposed to 5-fluorouracil (5-FU) in concentrations of 0, 0.05, 0.1, 1.0 and 5.0 µM, and concentrations of $^{90}Y$-huBrE-3 in concentrations of 0, 1.0, 2.0, and 4

μCi. Effects on proliferation were monitored after 72 hours using a commercially available MTT assay.

Similarly, SKOV-3 ovarian carcinoma cells were incubated with or without PABA at 0.1 mg/ml in DMEM for 3 days and subsequently exposed to topotecan at concentrations of 0, 0.1, 0.5 and 2.0 μM, and $^{90}$Y-huBrE-3 at concentrations of 0, 1.0, 2.0, and 4.0 μCi, and evaluated using an MTT assay after 72 hrs.

Results

Figure 6:
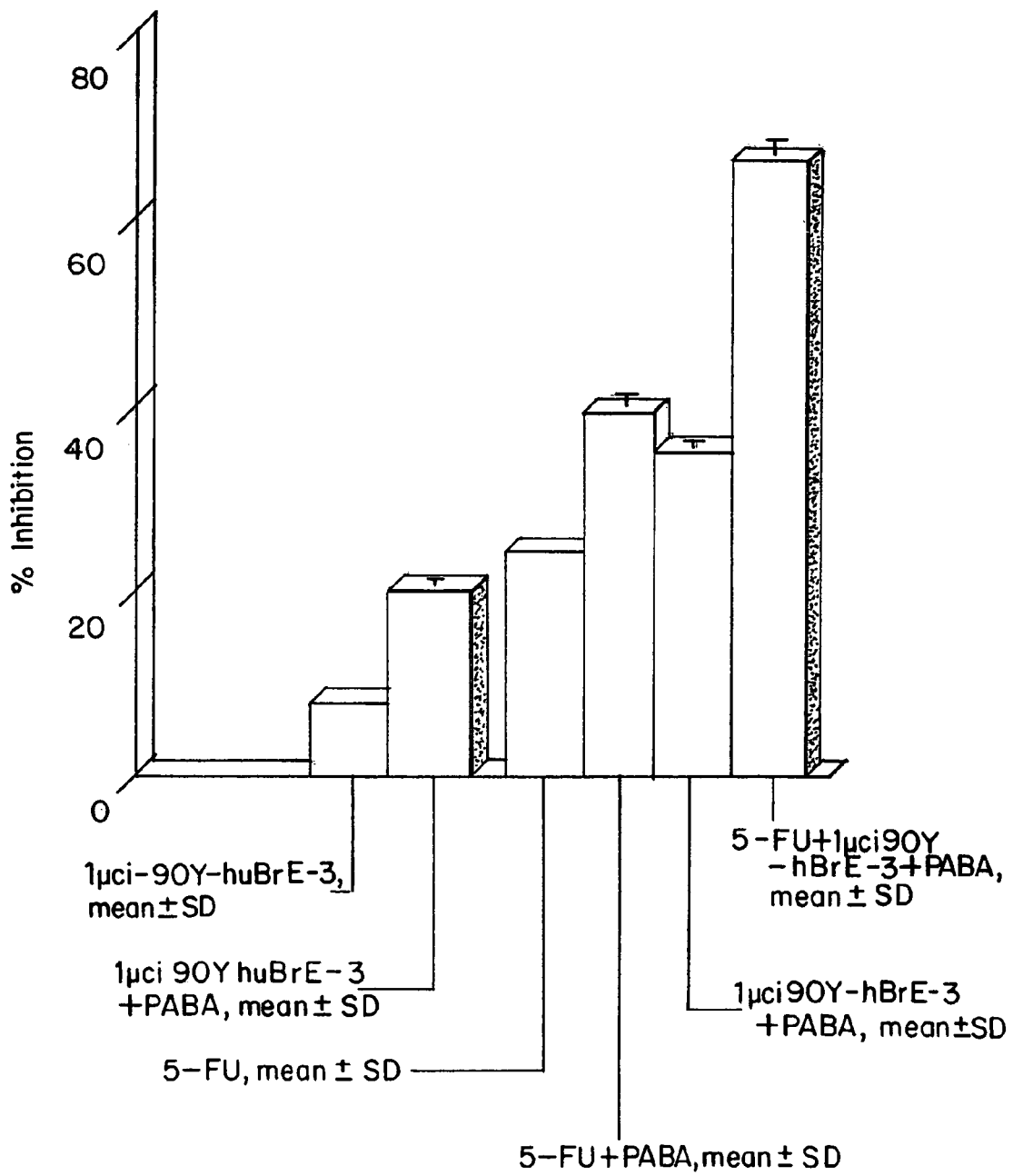
FIG. 6.

FIG. 6 shows that while 1 μCi of $^{90}$Y-huBrE-3 alone inhibited proliferation minimally, 1 μCi of $^{90}$Y-huBrE-3 in addition to PABA nearly tripled the inhibition. In addition, while 1 μM of 5-FU alone inhibited proliferation by about 25%, the combination of PABA and 1 μM 5-FU inhibited proliferation by 40%, and the combination of 1 μCi of $^{90}$Y-huBrE-3 and PABA inhibited proliferation by about 35%. Moreover, the combination of 1 μM of 5-FU, 1 μCi of $^{90}$Y-huBrE-3 and PABA inhibited proliferation by about 70%.

Figure 7:
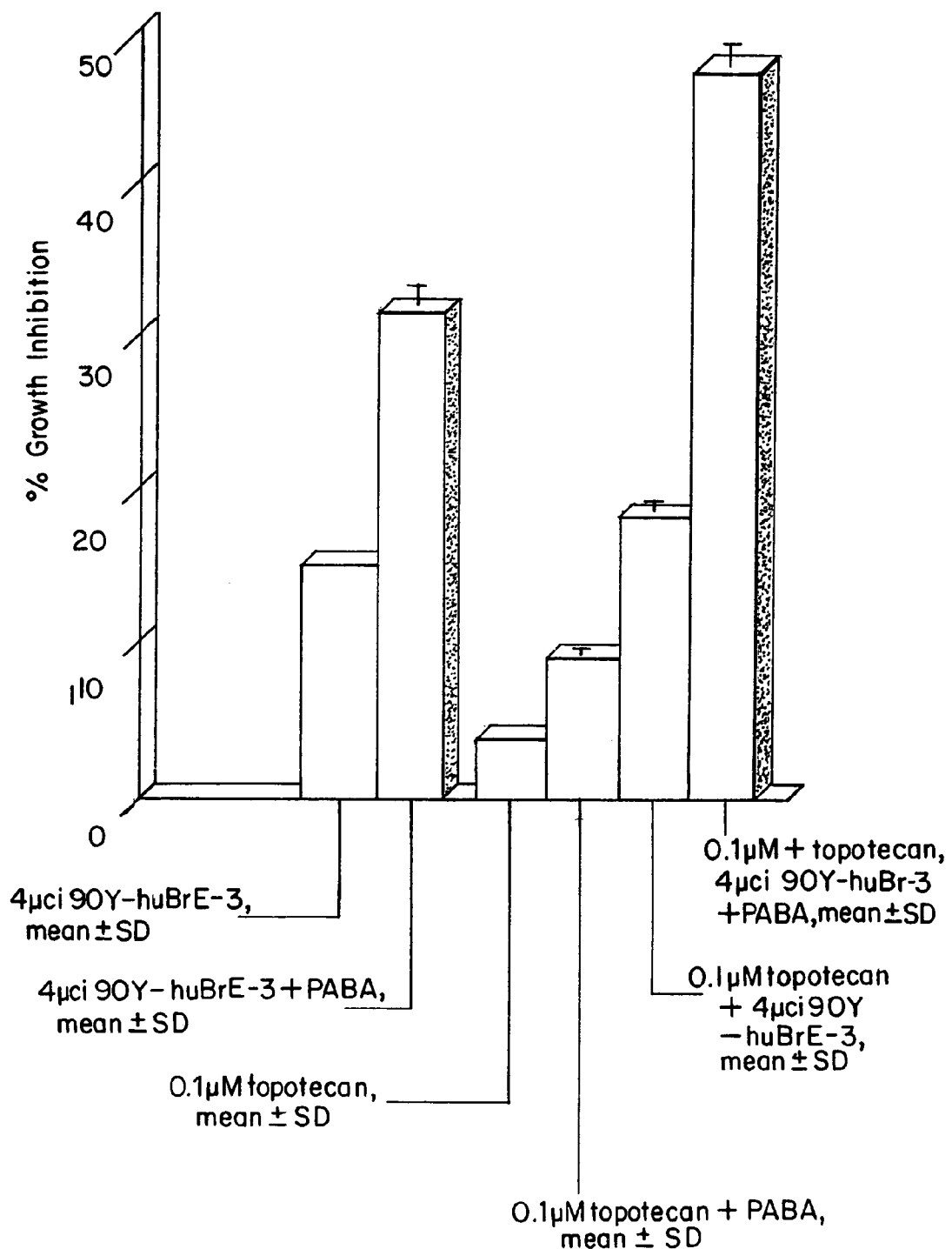
FIG. 7.

FIG. 7 shows that the addition of 4 μCi of $^{90}$Y-huBrE-3 alone inhibited SKOV-3 cell proliferation by about 15%, while the combination of PABA and 4 μCi of $^{90}$Y-huBrE-3 inhibited proliferation by more than 30%. Further, while addition of 0.1 uM topotecan inhibited proliferation minimally compared to untreated controls, treatment with 0.1 μM topotecan and PABA inhibited proliferation by about 10%, and treatment of 0.1 μM topotecan and 4 μCi $^{90}$Y-huBrE-3 inhibited proliferation by about 20%. The combination of 0.1 μM topotecan, 4 μCi $^{90}$Y-huBrE-3, and PABA was superior to the other combinations and inhibited proliferation of SKOV-3 cells by almost 50%.

Example 6

Standard or Recommended Treatment Regimens Contemplated for Use with PABA

Following are examples of treatment regimens for six cancers which are contemplated for use in conjunction with PABA according to the methods of the present invention. While treatment choices for each person with the following cancers depend on the type and stage of the cancer and the size and location of the tumor, below is an overview of typical treatment options/regimens.

A. Treatment Options for Breast Cancer. For invasive breast cancer, all types may be treated with breast-conserving surgery (mastectomy) plus radiation therapy or mastectomy. Radiation therapy consists of postoperative external-beam radiation to the entire breast with doses of 45 Gy to 50 Gy, in 1.8 Gy to 2.0 Gy daily fractions over a 5 week period. Shorter hypofractionation schemes achieve comparable results (Whelan et al., J Natl Cancer Inst. 2002; 94 (15): 1143-50).

RT and CT. Published results of three clinical trials found an overall survival advantage for combined chemotherapy and radiation therapy with prolonged follow-up. In the Danish Breast Cancer Cooperative Group 82b study, 1708 premenopausal women who were node-positive, T3 N0, or who had skin or pectoral fascial invasion were randomized to receive either cyclophosphamide, methotrexate, and 5-fluorouracil (5-FU) (collectively "CMF") and radiation therapy, or CMF alone after mastectomy (Overgaard et al., Danish Breast Cancer Cooperative Group 82b Trial. N Engl J Med 1997; 337 (14): 949-55). At 10 years, local-regional recurrence (9% versus 32%, P<0.001) and overall survival (54% versus 45%, P<0.001) favored the combined treatment arm.

The same group also studied postmenopausal women with stage II or stage III breast cancer. Six hundred eighty-six women were randomized to receive postoperative radiation therapy to the chest wall and regional lymph nodes plus tamoxifen (30 mg daily for 1 year), while 689 women received only tamoxifen. At a median follow-up of 10 years, local-regional recurrence (8% versus 35%, P<0.001) and overall survival (45% versus 36% at 10 years, P=0.03) favored the combined treatment (Overgaard et al., Lancet 19991; 353 (9165): 1641-8).

Tamoxifen. Tamoxifen is a drug that interferes with the hormone estrogen, and has been widely used to treat breast tumors, especially early-stage breast cancer and tumors expressing the estrogen receptor. A meta-analysis of systemic treatment of early breast cancer by hormone, cytotoxic, or biologic therapy methods in randomized trials involving 75,000 women with stage I or II breast cancer was performed. This analysis, which included information on 37,000 women in 55 trials of adjuvant tamoxifen, was published in 1998 (Breast Cancer Trialists' Collaborative Group. Lancet 1998; 351 (9114): 1451-67). In this analysis, the benefit of tamoxifen was found to be restricted to women with estrogen receptor (ER)-positive or ER-unknown breast tumors.

Tamoxifen and CT. In a trial of node-positive women older than 50 years of age with hormone receptor-positive tumors, 3-year disease-free and overall survival rates were better in those who received doxorubicin, cyclophosphamide, and tamoxifen versus tamoxifen alone (disease-free survival was 84% versus 67%, P=0.0004; overall survival was 93% versus 85%, P=0.04) (National Surgical Adjuvant Breast and Bowel Project B-23. J Clin Oncol 2001; 19 (4): 931-42).

Aromatase inhibitors. Aromatase inhibitors such as anastrozole and letrozole, in combination with tamoxifen, have been shown to result in longer disease-free survival compared with tamoxifen alone. (Nabholz et al., Clin Oncol 2000; 18(22): 3758-67).

RIT. In another report, the effect of $^{131}$I-labeled humanized anti-Lewis$^y$ monoclonal antibody 3S193 (hu3S193) was compared with that of placebo and radiolabeled huA33 control antibody in a series of radioimmunotherapy experiments in a MCF-7 xenografted BALB/c nude mouse breast cancer model (Clark et al., Clinical Cancer Research 2000; 6: 3621-3628). At 200 μCi/mouse, three of six mice that received $^{131}$I-hu3S193 showed significant tumor growth inhibition in contrast to no responses in the comparable placebo groups. The synergistic effects of RIT and chemotherapy was also evaluated using a combination of $^{131}$I-labeled hu3S193 antibody and TAXOL® using subtherapeutic doses of each agent. The combination of TAXOL® and 100 μCi of $^{131}$I-hu3S193 produced significant tumor inhibition in 80% of mice, whereas no responses were seen with either treatment modality alone or the combination of TAXOL® and a labeled control antibody.

In yet another report, the alpha emitting radioisotopes Tb-149 and Bi-213 were chelated to cancer specific monoclonal antibodies to form alpha-immunoconjugates (AIC) against melanoma, leukemia, prostate and colorectal cancer, and to the plasminogen activator inhibitor type-2 (PAI2) to form alpha-PAI2 (API) against breast and prostate cancer (Allen et al., Crit Rev Oncol Hematol. 2001;39(1-2):139-46). These conjugates were found to be highly stable, specific and cytotoxic in vitro. Melanoma and breast cancer tumor growth was observed in nude mouse models for untreated controls and non-specific AIC/API at 2 days post-subcutaneous inoculation of cancer cells. Complete inhibition of melanoma and breast cancer growth was found for local injections of AIC and API, respectively. Intra-lesional therapy of established melanoma showed that all melanomas regressed with 100 μCi injections of AIC.

Although RIT has not yet been approved for use to treat solid tumors, there has promising pre-clinical and clinical data. In one report single injection of Y-90-labeled MXDTPA-humanized-BrE-3 followed by autologous hematopoietic stem cells support in patients with refractory metastatic breast cancer was followed by systemic G-CSF (Cagnoni et al., Cancer Detection and Prevention 1998; 22 (Supplement 1). Two sets of patients received doses of $^{90}$Y of 10 mCi/meter squared (n=3) and 20 mCi/meter squared (n=3). Responses were: 1 partial response, 1 mixed response, 1 minimal response, 2 clinical improvement (no measurable disease). According to the present invention, PABA can be added to a regimen comprising, e.g., $^{90}$Y-huBrE-3 and XELODA® (capecitabine); or a regimen comprising e.g., $^{90}$Y-huBrE-3, topotecan, and PABA.

B. Treatment Options for Ovarian Cancer. Since ovarian cancer is often asymptomatic in its early stages, most patients have widespread disease at the time of diagnosis. Partly as a result of this, yearly mortality in ovarian cancer is approximately 65% of the incidence rate. Current treatment options (following surgery) include intraperitoneal P-32 or radiation therapy (Vergote, Cancer 1992; 69 (3): 741-9); systemic chemotherapy, e.g., with cisplatin (Vergote, supra); and total abdominal and pelvic radiation therapy (Dembo et al., Int J Radiat Oncol Biol Phys 1992; 22 (5): 835-45).

For Stage II ovarian cancer, systemic chemotherapy following surgery that comprises: paclitaxel (TAXOL®)+cisplatin or carboplatin (Trimble et al., J Clin Oncol 1993; 11 (12): 2405-10); cyclophosphamide+cisplatin (Decker et al., Obstet Gynecol 1982; 60 (4): 481-7); or; cyclophosphamide+carboplatin (Trask et al., J Clin Oncol 1991; 9 (7): 1131-7). For Stage III and IV ovarian cancer, the use of intraperitoneal cisplatin or carboplatin in conjunction with chemotherapy is recommended based on results of clinical trials. See e.g., Muggia et al., J Clin Oncol. 2000; 18(1):106-15 (paclitaxel and cisplatin); Harper et al., Semin Oncol. 2002; 29(3 Suppl 8):3-6 (paclitaxel and carboplatin); Semin Oncol. 1996; 23(5 Suppl 12):40-7 and Int J Gynecol Cancer. 2003; 13 Suppl 2:144-8 (cycloposphamide and cisplatin v. paclitaxel and cisplatin).

RIT. A Phase I trial of $^{90}$Y-CC49 RIT was conducted in twenty ovarian cancer patients who had persistent or recurrent intra-abdominal disease, had failed one or two prior chemotherapy regimens, and demonstrated TAG-72 expression (Alverez et al., Clin Cancer Res. 2002;8(9):2806-11). Patients were treated with intraperitoneal $^{90}$Y -CC49 given in combination with s.c. IFN alpha2b (dose of 3×10(6) units for a total of four doses) and intraperitoneal paclitaxel (dose of 100 mg/m²). The maximum tolerated dose of intraperitoneal $^{90}$Y -CC49 was established at 24.2 mCi/m² in this combined regimen. Of nine patients with measurable disease, two had partial responses lasting 2 and 4 months. Of 11 patients with nonmeasurable disease, median time to progression was 6 months in 7 patients who recurred; 4 of these patients had no evidence of disease at 9, 18, 19, and 23+ months.

Another Phase I study evaluated $^{177}$Lu-CC49 in patients with recurrent or persistent ovarian cancer confined to the abdominal cavity, alone or in combination with interferon and TAXOL (34 patients) (Cancer Biother Radiopharm. 2001; 16(4): 305-15). The maximum tolerated dose for $^{177}$Lu-CC49 was 40 mCi/m2 when given with IFN+100 mg/m2 TAXOL. Four of 17 patients with CT measurable disease had a partial response (PR) and 4 of 27 patients with non-measurable disease have progression-free intervals of 18+, 21+, 21+, and 37+ months.

C. Treatment Options for Glioblastoma. Glioblastoma multiform is grade IV astrocytoma which is poorly differentiated and grows rapidly. For glioblastoma multiforme, the cure rate is very low with standard local treatment. For resectable tumors, surgery in addition to radiation therapy (external beam) and chemotherapy (e.g., BCNU) is recommended (Selker et al., Neurosurgery 2002; 51 (2): 343-55). For unresectable tumors, clinical trials that evaluate hyperfractionated irradiation, accelerated fraction irradiation, stereotactic radiosurgery, radiosensitizers, hyperthermia, interstitial brachytherapy, or intraoperative radiation therapy used in conjunction with external-beam radiation therapy to improve local control of the tumor and/or studies that evaluate new drugs and biological response modifiers following radiation therapy (Fontanesi et al., Am J Clin Oncol 16 (5): 412-7, 1993).

RIT. Some success has been achieved using RIT in glioblastoma patients. Since 1995, 37 patients were treated with radioimmunotherapy after resection and radiotherapy of a malignant glioma (24 glioblastoma) (Goetz et al., J Neurooncol. 2003 May; 62(3):321-8). Patients received antibodies labeled with $^{90}$Y and $^{131}$I in different doses into the tumor cavity via a previously implanted ommaya-reservoir. Treatment was applied in up to 8 cycles (mean 2.96 cycles) in time intervals of 6-8 weeks. Radioimmunotherapy prolonged survival time in a selected group of patients with malignant gliomas as compared to a historical control group.

D. Treatment Options for Pancreatic Cancer. Surgical resection is recommended, alone or in conjunction with postoperative 5-fluorouracil (5-FU) and regional split course radiation given at a dose of 40 Gy (Gastrointestinal Tumor Study Group. Cancer 1987; 59 (12): 2006-10).

In 2002, the Radiation Therapy Oncology Group completed a prospective, randomized trial to evaluate whether gemcitabine chemotherapy administered prior to and following external beam radiation with concurrent 5-FU is superior to adjuvant 5-FU for patients with completely resected tumors; preliminary analysis is pending.

RIT. Significant antitumor effects have been demonstrated in animal models using radiolabeled PAM4 for RIT. One study demonstrated improved anti-tumor activity of low-dose $^{90}$Y-PAM4 in combination with gemcitabine with minimal toxicity (Clin Cancer Res. 2003;9(10 Pt 2):3929S-37S).

E. Treatment Options for Colon Cancer. Colon cancer is highly treatable with surgery, but recurrence is often a problem. The prognosis of colon cancer is clearly related to the degree of penetration of the tumor through the bowel wall and the presence or absence of nodal involvement. Treatment options normally consist of systemic adjuvant chemotherapy employing fluorouracil (5-FU) in conjunction with either levamisole or leucovorin (Moertel, N Engl J Med 1990; 322 (6): 352-8). For locally advanced disease, radiation therapy with chemotherapy is currently being evaluated. A study comparing 5-FU and leucovorin with fluorouracil/semustine/ vincristine has demonstrated a statistically significant benefit in both survival and disease-free survival for the 5-FU/leucovorin arm (Wolmark et al., Clin Oncol 1993; 11 (10): 1879- 87). For the most severe cases of colon cancer (i.e., metastatic, stage IV) other chemotherapeutic agents such as irinotecan (CPT-11), raltitrexed, capecitabine, and oxaliplatin can be used as a substitute for, or in combination with, 5-FU, with or without other agents.

RIT. Combinations of radiolabeled antibodies, or pre-targeting of radiolabeled antibodies and chemotherapy in xenografts of human colon cancer cells in nude mice has been observed by several groups (Graves et al., Clin Cancer Res. 2003; 9:3712-21; Mayr et al., Cancer Invest. 2003 June; 21(3):382-8; and Kinuya et al., Cancer Sci. 2003 July; 94(7): 650-4).

F. Treatment Options for Lung Cancer. Lung cancer is primarily in one of two forms, non-small cell lung carcinoma (NSCLC) and small-cell lung carcinoma (SCLC). For NSCLC, standard treatment yields poor results in all but the most localized growths. All newly diagnosed patients with NSCLC are potential candidates for studies evaluating new forms of treatment. Current areas under evaluation include combinations of surgery, radiation therapy, chemotherapy and immunotherapy in an effort to develop more effective systemic therapy. Several agents, including paclitaxel (TAXOL®), docetaxel (TAXOTERE®), topotecan, irinotecan, vinorelbine, and gemcitabine have been shown to be active in the treatment of advanced NSCLC (Pastorino et al., J Clin Oncol, 1993; 11(7): 1216-22). Patients with inoperable stage II disease should be treated with radiation therapy consisting of approximately 6,000 cGy delivered with megavoltage equipment to the midplane of the volume of known tumor using conventional fractionation.

For Stage III and IV NSCLC, post-operative cisplatin or carboplatin regimens along with radiation is standard treatment. Reports of taxane/platinum combinations, e.g., paclitaxel and carboplatin, docetaxel and cisplatin, gemcitabine and cisplatin, have also shown relatively high response rates (Johnson et al., J Clin Oncol 1996; 14 (7): 2054-60; Schiller et al., Proceedings of the American Society of Clinical Oncology 19: A-2, 1a, 2000).

Small cell lung carcinoma (SCLC) has the most aggressive clinical course of any type of pulmonary tumor, with median survival from diagnosis of only 2 to 4 months. For limited stage SCLC, combined modality treatment with radiation and chemotherapy is recommended, e.g., radiation doses in the range of 4,000 to 4,500 cGy or more (standard fractionation), with etoposide and carboplatin (Murray et al., J Clin Oncol 1993; 11 (2): 336-44). For extensive SCLC, radiation and combination chemotherapy comprising the following combinations have resulted in complete responses: cyclophosphamide+doxorubicin+vincristine (Feld et al., J Clin Oncol 1984; 2 (4): 294-304); cyclophosphamide+doxorubicin+etoposide (Aisner et al., Cancer Treat Rep 1982; 66 (2): 221-30); etoposide+cisplatin or carboplatin (Skarlos et al., Ann Oncol 1994; 5 (7): 601-7); ifosfamide+carboplatin+etoposide (Thatcher et al., Lung Cancer 1993; 9(Suppl 1):s51-S67).

RIT. In one study, 16 patients with NSCLC enrolled in a phase I trial of $^{90}$Y-CC49 monoclonal therapy were treated with post-RIT salvage chemotherapy. The majority of these patients were treated with doses of $^{90}$Y of >/=14 mCi/m(2) (8-20 mCi/m(2)), and four of them received concurrent 96-hour Taxol infusion. The resulting data suggested that therapy with RIT did not significantly affect survival of these patients. Accordingly, there remains a need in the art for combined modality regimens with enhanced efficacy.

G. Treatment Options for Sarcomas. Sarcomas are a general category of tumors originating from mesodermal tissues of the extremities, trunk and retroperitoneum, head and neck, and, rarely, in the gastrointestinal tract or gastrointestinal stroma. Patients with sarcoma often require a combination of surgery, chemotherapy and radiation therapy to maximize functional results, improve local control, and optimize overall survival. Surgery is recommended, although the benefits of adjuvant chemotherapy have not been conclusively established except for advanced sarcoma, for which doxorubicin alone or with dacarbazine is considered the best chemotherapeutic regimen (Santoro et al., J Clin Oncol 1995; 13 (7): 1537-45). For metastatic sarcomas, additional treatment with ifosfamide and mesna can be employed (J Clin Oncol 1993; 11 (7): 1276-85). For tumors tumor larger than 5 centimeters in diameter or Stage IV tumors, surgical excision followed by radiation therapy is generally performed.

RIT. Preclinical evaluation of radiolabeled antibodies as monotherapy, or in combination with external radiation or chemotherapy in mouse xenografts of human sarcomas has demonstrated that use of this therapy may be therapeutically efficacious (Wakai et al., Jpn J Cancer Res. 2000;91(12): 1319-25; Leigh et al., Cancer Biother Radiopharm. 1999; 14(2):113-9; and Larsen et al., Br J Cancer. 1998; 77(7):1115-22).

H. Treatment Options for Non-Hodgkin's Lymphoma. Disease control can be achieved in a significant number of patients with indolent stage I or stage II NHL by using doses of radiation that usually range from 2500 to 4000 cGy to involved sites, or to extended fields which cover adjacent nodal sites. Two large randomized prospective trials document a better outcome with a combination of cyclophosphamide+doxorubicin+vincristine+prednisone and radiation therapy over chemotherapy alone (Miller et al., N Engl J Med 1988; 339 (1): 21-6; and Glick et al., Proceedings of the American Society of Clinical Oncology 1995; 14: A-1221, 391-abstract).

For advanced stage The treatment of choice for patients with advanced stages of aggressive non-Hodgkin's lymphoma (NHL) is combination chemotherapy, either alone or supplemented by local-field irradiation (Armitage et al., N Engl J Med 1993; 328 (14): 1023-30.) The following are exemplary chemotherapy regimens:

CHOP: cyclophosphamide+doxorubicin+vincristine+prednisone.

CNOP: cyclophosphamide+mitoxantrone+vincristine+prednisone.

m-BACOD: methotrexate+bleomycin+doxorubicin+cyclophosphamide+vincristine+dexamethasone+leucovorin.

MACOP-B: methotrexate+doxorubicin+cyclophosphamide+vincristine+prednisone fixed dose+bleomycin+leucovorin.

ProMACE CytaBOM: prednisone+doxorubicin+cyclophosphamide+etoposide+cytarabine+bleomycin+vincristine+methotrexate+leucovorin.

The combination of rituximab and CHOP has shown improvement in event-free survival and overall survival (Coiffier et al., N Engl J Med 2002; 346 (4): 235-42).

Treatment of adult lymphoblastic lymphoma, an aggressive form of Non-Hodgkin's lymphoma, includes systemically administered combination chemotherapy with CNS preventive therapy. CNS prophylaxis is achieved with chemotherapy (intrathecal and/or high-dose systemic) and, in some cases, cranial irradiation. Most current induction regimens for adult acute lymphoblastic leukemia (ALL) include prednisone, vincristine, and an anthracycline. Some regimens also add other drugs, such as asparaginase or cyclophosphamide (Larson et al., Blood 1995;85 (8): 2025-37). Supportive care during remission induction treatment should routinely include red blood cell and platelet transfusions when appropriate.

RIT. Treatment with $^{131}$I-labeled anti-CD20 (BEXXAR®) or $^{90}$Y-labeled or $^{111}$In-labeled anti-CD20 (ibritumomab-ZEVALIN®) is approved for the treatment of CD20-positive Non-Hodgkin's lymphoma whose disease is refractory to Rituximab and has relapsed following chemotherapy. The ZEVALIN® therapeutic regimen is administered in two steps: Step 1 includes one infusion of Rituximab preceding infusion of In-111 ZEVALIN®. Step 2 follows Step 1 by seven to nine days and consists of a second infusion of Rituximab followed by Y-90 ZEVALIN®. The BEXXAR treatment regimen comprises a first infusion with tositumomab, followed by an infusion with $^{131}$I-I tositumomab, repeated after 7-14 days.

Example 6

PABA Alters Expression of Cell Cycle Control Genes in Tumor Cells

Figure 8:
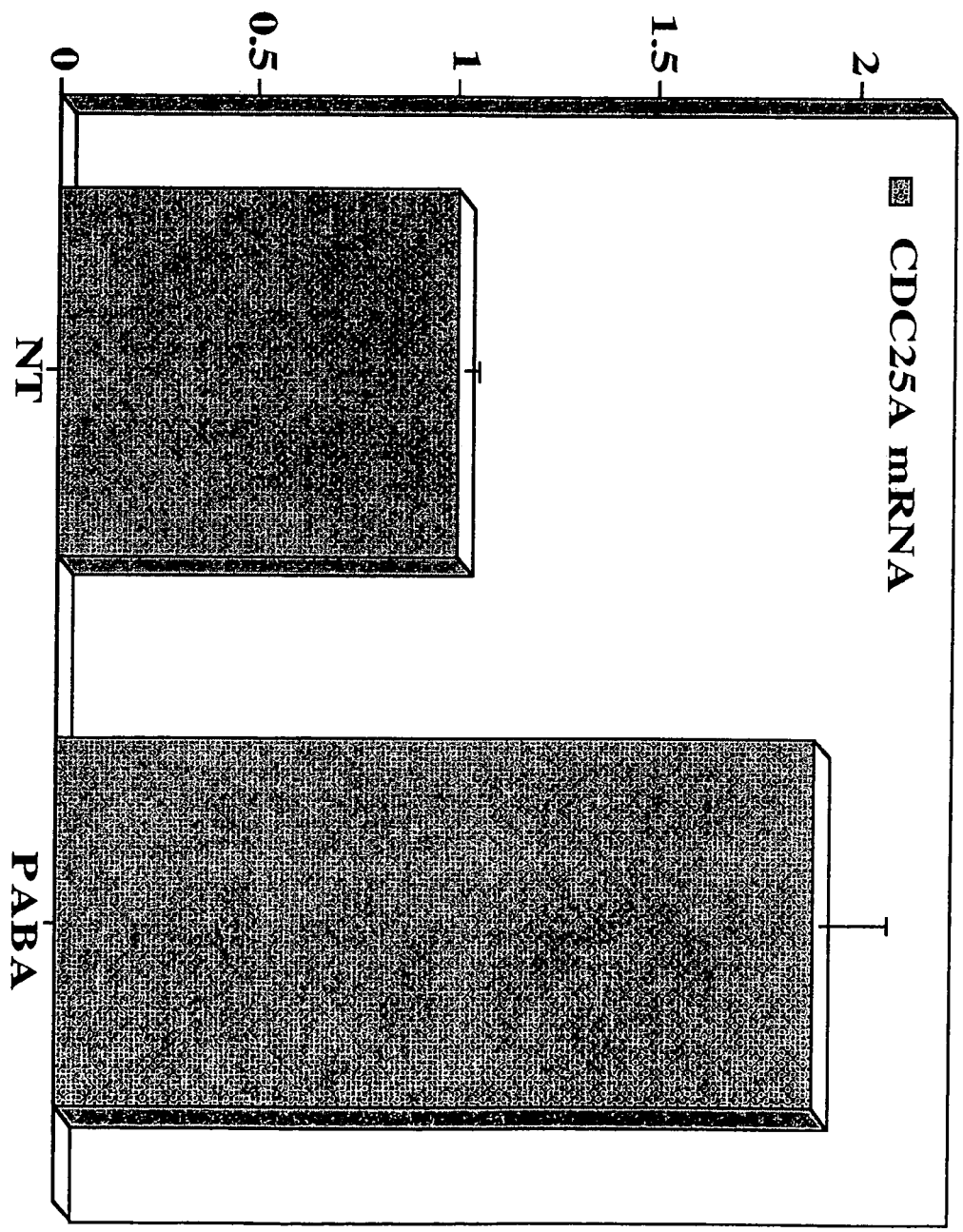
FIG. 8.

An AFFYMATRIX™ based cDNA array analysis was performed on tumor cells cultured in the presence or absence of PABA (100 µg/ml). A number of genes within the tumor cells were differentially expressed following PABA treatment. Experiments were conducted on genes that were consistently altered in both human and mouse tumor cells. The cell cycle regulatory proteins c-Myc, CDC25A, Id-1, Id-2, and Id-3 were all up-regulated by about 2 to about 5 fold in both B16F10 and G361 melanoma cells. In contrast, P21$^{CIP1}$, BRCA-2 and H2A and H2B histone genes were down-regulated following PABA treatment. To confirm these findings, the expression of CDC25A was analyzed. 4T1 breast carcinoma cells and B16F10 melanoma cells were incubated in the presence or absence of PABA. After 7 days, the RNA was isolated. The relative levels of CDC25A mRNA were examined by RT-PCR or real time PCR. FIG. 8. Treatment of 4T1 breast carcinoma cells and melanoma cells with PABA resulted in increase in the levels of CDC25A of about 2 fold compared to untreated controls as measured by RT-PCR.

Western blot analysis was performed to confirm the altered expression of CDC25A, c-Myc and BRCA-2 at the protein level. G361 melanoma cells were cultured for 2 weeks in the presence or absence of PABA. The cells were harvested and lysed in 1.0% Triton-X-100 lysis buffer. Equal amounts of total cell lysates (50 µg/lane) were separated by 10% SDS PAGE and the proteins were transferred to nitrocellulose membranes. The membranes were probed with monoclonal antibodies P4C10 (anti-β1 integrin), 3303 (anti-BRCA-2) and Ab-3 (anti-CDC25A) or secondary antibody only. Tumor cells treated with PABA showed no change in the expression of β1 integrin subunit compared to cells grown in the absence of PABA. BRCA-2 expression was decreased in cells treated with PABA compared to cells grown in the absence of PABA. CDC25A expression was markedly increased in cells treated with PABA compared to cells grown in the absence of PABA. In similar studies, c-Myc expression in 4T1 breast carcinoma cells and G361 melanoma cells was examined by Western blot. The nitrocellulose membranes were probed with anti-c-Myc monoclonal antibody 9402 (available from Cell Signaling Technology, Beverly, Mass.) and anti-actin monoclonal antibody. Treatment of both the 4T1 cells and G361 cells with PABA resulted in significant up-regulation of c-Myc compared to untreated cells. No change in actin levels was observed.

These results show that treatment of cancer cells with PABA results in differential expression of CDC25A, c-Myc and BRCA-2 compared to untreated cells.

Example 7

PABA Alters Expression of Cell Cycle Dependent Kinase Inhibitor P21$^{CIP1}$ in Tumor Cells P21$^{CIP1}$ is a cell cycle dependent kinase inhibitor, which has a role in regulating the sensitivity of breast cancer cells to chemotherapeutic agents such as TAXOL®. 4T1 breast cancer cells were incubated in the presence or absence of PABA (100 µg/ml) for 7 days. The cells were washed and cell lysates were prepared. Levels of P21$^{CIP1}$ were analyzed by Western blot. Equal amounts (50 µg/lane) were separated by SDS PAGE and transferred to nitrocellulose membranes. The membranes were probed with anti-P21$^{CIP1}$ or anti-actin monoclonal antibodies. The cells treated with PABA had significantly reduced levels of P21$^{CIP1}$ compared to untreated cells. Little change was observed in the level of actin.

Example 8

PABA Promotes Accumulation of Tumor Cells in S Phase

G361 melanoma cells and 4T1 breast cancer cells were cultured in the presence or absence of PABA (100 µg/ml) for 2 weeks. The tumor cells were synchronized by serum starvation and cultured for 2 hours in 10% serum-containing medium. The cells were harvested, washed, fixed and stained with propidium iodide. Cell cycle analysis was performed by flow cytometry. The relative levels of untreated G361 cells (12%) and 4T1 cells (10%) in S-phase were low compared. FIG. 9. In contrast, 72% of PABA-treated G361 cells and 40% of PABA-treated 4T1 cells were in S-phase.

These results show that PABA treatment promotes accumulation of tumor cells in S-phase.

Example 9

PABA Increases the Levels of Reactive Oxygen Species in Tumor Cells

Figure 10:
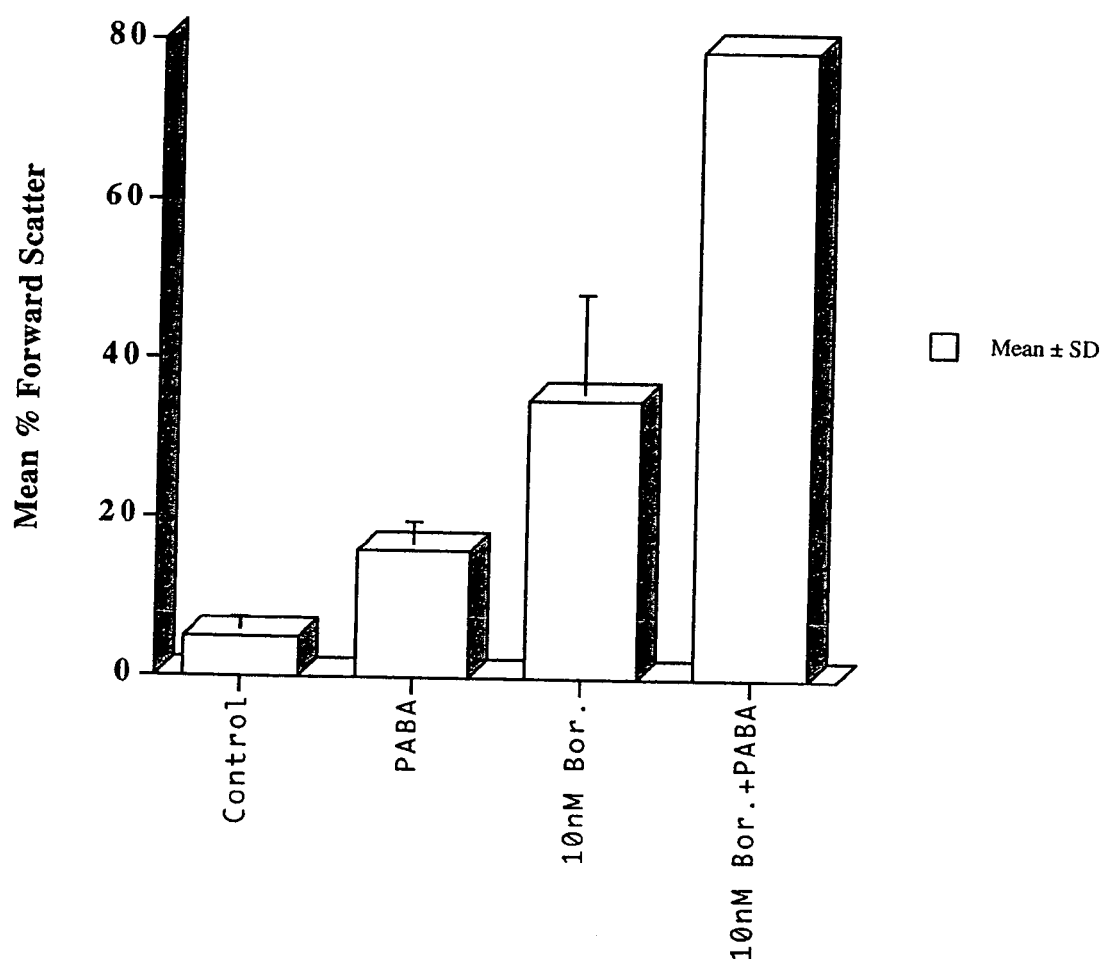
FIG. 10.

H460 non-small cell lung cancer cells were grown in the presence or absence of PABA (100 µg/ml) in RPMI-1640 media containing 10% fetal calves serum, 1% penn/strep and 1% NaPyruvate. After 24 hours, a portion of the cells were exposed to 0.01 bortezomib (10 nM) for an additional 24 hours. Bortezomib is a strong proteasome inhibitor that has been shown to actively induce reactive oxygen species (ROS) at a concentration of 100 nM after 24 hours exposure (Ling et al., J Biol Chem. 2003; 478:33714-33723). The cells were monitored for ROS by the addition of dihydrothidine at a concentration of 5 µM for 15 minutes followed by fixation in ethanol and analysis by FACS. The cells treated with PABA alone had a 3 fold increase in ROS compared to untreated cells. FIG. 10. Cells treated with PABA and bortezomib had about a 2 fold increase in ROS compared to cells treated with bortezomib alone.

These results show that PABA treatment alone increases the level of ROS in tumor cells compared to untreated tumor cells. PABA treatment also increases the level of ROS in bortezomib-treated tumor cells compared to tumor cells treated with bortezomib alone.

REFERENCE CITED

Numerous references, including patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entirety and to the same extent as if each reference was individually incorporated by reference.

What is claimed:

1. A method of treating non-melanotic cancer in a subject in need of such treatment comprising orally administering to the subject an effective amount of para-aminobenzoic acid (PABA) in combination with at least one of radiotherapy, radioimmunotherapy, or a chemotherapeutic agent selected from the group consisting of paclitaxel, docetaxel, carboplatin, vinorelbine, and gemcitabine; wherein the non-melanotic cancer is breast cancer.

2. A method of treating non-melanotic cancer in a subject in need of such treatment comprising orally administering to the subject an effective amount of para-aminobenzoic acid (PABA) in combination with at least one of radiotherapy, radioimmunotherapy, or a chemotherapeutic agent selected from the group consisting of paclitaxel, docetaxel, carboplatin, vinorelbine, and gemcitabine; wherein the non-melanotic cancer is non-small cell lung carcinoma.

3. A method of inhibiting metastasis of tumor cells comprising contacting the tumor cells with an effective amount of PABA in combination with chemotherapy, wherein the tumor cells are breast tumor cells and the chemotherapy is paclitaxel.

* * * * *